US012708613B2

(12) United States Patent
Larsen

(10) Patent No.: US 12,708,613 B2
(45) Date of Patent: Aug. 18, 2026

(54) METHODS FOR IMPROVING PHYSICAL EXERCISE PERFORMANCE

(71) Applicant: NOMIO NUTRITION AB, Stockholm (SE)

(72) Inventor: Filip Larsen, Stockholm (SE)

(73) Assignee: NOMIO NUTRITION AB, Stockholm (SE)

( * ) Notice: Subject to any disclaimer, the term of this patent is extended or adjusted under 35 U.S.C. 154(b) by 402 days.

(21) Appl. No.: 18/266,632

(22) PCT Filed: Dec. 13, 2021

(86) PCT No.: PCT/EP2021/085455
§ 371 (c)(1),
(2) Date: Jun. 12, 2023

(87) PCT Pub. No.: WO2022/128897
PCT Pub. Date: Jun. 23, 2022

(65) Prior Publication Data

US 2024/0108596 A1 Apr. 4, 2024

(30) Foreign Application Priority Data

Dec. 14, 2020 (GB) ..................................... 2019660

(51) Int. Cl.
*A61K 31/26* (2006.01)
*A61K 31/7028* (2006.01)
*A61K 36/31* (2006.01)
*A61K 38/47* (2006.01)
*A61P 3/02* (2006.01)

(52) U.S. Cl.
CPC .......... *A61K 31/26* (2013.01); *A61K 31/7028* (2013.01); *A61K 36/31* (2013.01); *A61K 38/47* (2013.01); *A61P 3/02* (2018.01); *C12Y 302/01147* (2013.01)

(58) Field of Classification Search
None
See application file for complete search history.

(56) References Cited

FOREIGN PATENT DOCUMENTS

WO WO 2012/074412 A1 6/2012
WO WO-2020225608 A1 * 11/2020 ......... A61K 31/7032

OTHER PUBLICATIONS

Fahey et al., "Sulforaphane Bioavailability from Glucoraphanin-Rich Broccoli: Control by Active Endogenous Myrosinase", PLOS One, vol. 10, article e0140963, pp. 1-13 (Year: 2015).*
Schiffer, T. A. et al., "Dynamic regulation of metabolic efficiency explains tolerance to acute hypoxia in humans," *The FASEB Journal*, 28 (2014): 4303-4311.
Singh, K. B. et al., "Reversal of the Warburg phenomenon in chemoprevention of prostate cancer by sulforaphane," *Carcinogenesis*, 40.12 (2019): 1545-1556.
Axelsson, A. S. et al., "Sulforaphane reduces hepatic glucose production and improves glucose control in patients with type 2 diabetes," *Science Translational Medicine*, 9 (2017): 1-12.
Malaguti. M. et al., "Sulforaphane treatment protects skeletal muscle against damage induced by exhaustive exercise in rats," *J Appl Physiol*., 107(2009): 1028-1036.
PCT International Search Report and Written Opinion issued in International Patent Application No. PCT/EP2021/085455, mailed Mar. 24, 2022.
Ruhee. R. T. et al., "Protective Effects of Sulforaphane on Exercise-Induced Organ Damage via Inducing Antioxidant Defense Responses," *Antioxidants*, 9 (2020): 1-15.
Ruhee, R. T. et al., "The Integrative Role of Sulforaphane in Preventing Inflammation, Oxidative Stress and Fatigue: A Review of a Potential Protective Phytochemical," *Antioxidants*, 9 (2020): 1-13.
Yagishita, Y. et al., "Broccoli or Sulforaphane: Is It the Source or Dose That Matters?," *Molecules*, 24 (2019): 1-38.
Bouranis, J. A. et al., "Sulforaphane and Sulforaphane-Nitrile Metabolism in Humans Following Broccoli Sprout Consumption: Inter-individual Variation, Association with Gut Microbiome Composition, and Differential Bioactivity," *Molecular Nitrition & Food Research*, 68.4 (2023), abstract only.
Egan, B. et al., "Molecular responses to acute exercise and their relevance for adaptations in skeletal muscle to exercise training," *Physiol Rev*., 103.3 (2023): 2057-2170, abstract only.
Hellsten, Y. et al., "Cardiovascular Adaptations to Exercise Training," *Compr Physiol*., 6.1 (2015): 1-32, abstract only.
Abukhabta, S. et al., "Sulforaphane-enriched extracts from glucoraphanin-rich broccoli exert antimicrobial activity against gut pathogens in vitro and innovative cooking methods increase in vivo intestinal delivery of sulforaphane," *Eur J Nutr*., 60 (2021): 1263-1276.
Alumkal, J. J. et al., "A phase II study of sulforaphane-rich broccoli sprout extracts in men with recurrent prostate cancer," *Invest New Drugs*, 33.2 (2015): 480-489.
Borg G. A. V. et al., "Psychophysical bases of perceived exertion," *Medicine and Science in Sports and Exercise*, 14.5, (1982): 377-381.
Cardinale, D. A. et al., "Reliability of maximal mitochondrial oxidative phosphorylation in permeabilized fibers from the vastus lateralis employing high-resolution respirometry," *Physiological Reports*, 6.4 (2018): e13611, 1-8.
Clarke, J. D. et al., "Comparison of isothiocyanate metabolite levels and histone deacetylase activity in human subjects consuming broccoli sprouts or broccoli supplement," *J Agric Food Chem*, 59.20 (2011): 10955-10963.
Dinkova-Kostova, A. T. et al., "KEAP1 and done? Targeting the NRF2 pathway with sulforaphane," *Trends in Food Science & Technology*, 69 (2017): 257-269.
Done, A. J. et al., "Aerobic exercise increases resistance to oxidative stress in sedentary older middle-aged adults. A pilot study," *Age*, 38 (2016): 505-512.

(Continued)

*Primary Examiner* — Michelle F. Paguio Frising
(74) *Attorney, Agent, or Firm* — pH IP Law

(57) ABSTRACT

The present invention relates to compositions, uses and methods for improving physical exercise performance, and/or improving adaptation to physical exercise, and/or modulating the concentration of lactate and/or glucose in the blood of a human subject.

24 Claims, 11 Drawing Sheets

(56) References Cited

OTHER PUBLICATIONS

Figure 1:
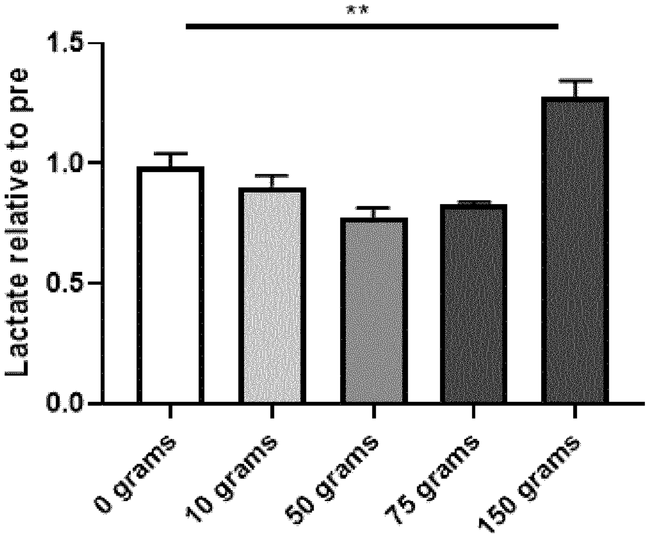

Hashimoto, T. et al., "Lactate sensitive transcription factor network in L6 cells: activation of MCT1 and mitochondrial biogenesis," *FASEB J.*, 21 (2007): 2602-2612.
Larsen, F. J. et al., "High-intensity sprint training inhibits mitochondrial respiration through aconitase inactivation," *FASEB J.*, 30 (2016): 417-427.
Larsen, S. et al., "Biomarkers of mitochondrial content in skeletal muscle of healthy young human subjects," *J Physiol.*, 590.14 (2012): 3349-3360.
López-Chillón, M. T. et al., "Effects of long-term consumption of broccoli sprouts on inflammatory markers in overweight subjects," *Clinical Nutrition*, 38 (2019):745-752.
Lu, T. et al., "Gene regulation and DNA damage in the ageing human brain," *Nature*, 429 (2004): 883-891.
Ludvik, B. et al., "Effects of dichloroacetate on exercise performance in healthy volunteers," *European Journal of Physiology*, 423 (1993): 251-254.
Mayes, R. et al., "The influence of training on endurance and blood lactate concentration during submaximal exercise," *Brit. J. Sports Med.*, 21.3 (1987): 119-124.
Meitinger, N. et al., "Development and validation of a quick assay for the total glucosinolate content in horseradish (*Armoracia rusticana*) using glucose strips and a blood glucose meter," *Journal of Applied Botany and Food Quality*, 91 (2018): 232-236.
Oh, S. et al., "Nuclear factor (erythroid derived 2)-like 2 activation increases exercise endurance capacity via redox modulation in skeletal muscles," *Science Reports*, 7 (2017): 12902, 1-11.
Poffé, C. et al., "Ketone ester supplementation blunts overreaching symptoms during endurance training overload," *J Physiol.*, 12 (2019): 3009-3027.
Ristow, M. et al., "Antioxidants prevent health-promoting effects of physical exercise in humans," *PNAS*, 106.21 (2009): 8665-8670.
Samuelsson, H. et al., "Intake of branched-chain or essential amino acids attenuates the elevation in muscle levels of PGC-1a4 mRNA caused by resistance exercise," *Am J Physiol Endocrinol Metab.*, 311 (2016): E246-E251.
Singh, K. et al., "Sulforaphane treatment of autism spectrum disorder (ASD)," *PNAS*, 111.43 (2014): 15550-15555.
Sutherland, L. N. et al., "Exercise and adrenaline increase PGC-1$\alpha$ mRNA expression in rat adipose tissue," *J Physiol.*, 587.7 (2009): 1607-1617.
Wang, L. et al., "Nrf2 Activation Enhances Muscular MCT1 Expression and Hypoxic Exercise Capacity," *Medicine & Science in Sports & Exercise*, 52.8 (2020): 1719-1728.
Wilkinson, A. P. et al., "Determination of Myrosinase (Thioglucoside Glucohydrolase) activity by a spectrophotometric coupled enzyme assay," *Analytical Biochemistry*, 139 (1984): 284-291.
Wise, R.A. et al., "Lack of Effect of Oral Sulforaphane Administration on Nrf2 Expression in COPD: A Randomized, Double-Blind, Placebo Controlled Trial," *PLoS One*, 11.11 (2016): 1-15.
Bernal, W. et al., "Blood lactate as an early predictor of outcome in paracetamol-induced acute liver failure: a cohort study," *Lancet*, 359.9306 (2002): 558-563 (abstract only).
Cheng, S. et al., "Lactate and lactylation in liver diseases: energy metabolism, inflammatory immunity and tumor microenvironment," *Front Immunol.*, 16 (2025): 1581582 (abstract only).
De Vriese, An. S. et al., "Linezolid-induced inhibition of mitochondrial protein synthesis," *Clin Infect Dis.*, 42.8 (2006): 1111-1117 (abstract only).
Drolz, A. et al., "Lactate Improves Prediction of Short-Term Mortality in Critically Ill Patients With Cirrhosis: A Multinational Study," *Hepatology*, 69.1 (2019): 258-269 (abstract only).
Kowlgi N. G. et al., "D-lactic acidosis: an underrecognized complication of short bowel syndrome," *Gastroenterol Res Pract.*, (2015): 476215 (abstract only).
Lee, Y-S. et al., "Correlation between regional tissue perfusion saturation and lactate level during cardiopulmonary bypass," *Korean J. Anesthesiol.*, 71.5 (2018): 361-367 (abstract only).
Levy, B. et al., "Increased muscle-to-serum lactate gradient predicts progression towards septic shock in septic patients," *Intensive Care Med.*, 36.10 (2010): 1703-1709 (abstract only).
Masharani, U. et al., "Hyperlactatemia in diabetic ketoacidosis," *Diabet Med.*, 39.4 (2022): e14723 (abstract only).
Ortega-Sáenz, P. et al., "Selective accumulation of biotin in arterial chemoreceptors: requirement for carotid body exocytotic dopamine secretion," *J Physiol.*, 594.24 (2016): 7229-7248 (abstract only).
Protti, A. et al., "Oxygen consumption is depressed in patients with lactic acidosis due to biguanide intoxication," *Crit. Care*, 14.1 (2010): R22 (abstract only).
Ruan, G. J. et al., "Elevated Serum Lactate in Patients With Lymphoma: It Is Not Always Infection," *Mayo Clin Innov Qual Outcomes*, 5.2 (2021): 423-430 (abstract only).
Sproule, D. M. et al., "Mitochondrial encephalopathy, lactic acidosis, and strokelike episodes: basic concepts, clinical phenotype, and therapeutic management of MELAS syndrome," *Ann N Y Acad Sci.*, 1142 (2008): 133-158 (abstract only).
Takahashi, T. et al., "Severe perioperative lactic acidosis in a pediatric patient with glycogen storage disease type Ia: a case report," *JA Clin Rep.*, 9.1 (2023): 91 (abstract only).
Tonsgard, J. H. et al., "Lactic acidemia in Reye's syndrome," *Pediatrics*, 69.1 (1982): 64-69 (abstract only).
Le, T. N. et al., "Broccoli (*Brassica oleracea* L. var. *italica*) Sprouts as the Potential Food Source for Bioactive Properties: A Comprehensive Study on In Vitro Disease Models," *Foods*, 8. 532 (2019): 8110532, 1-14.
Office Action issued in Japanese Patent Application No. 2023-559158, dated Feb. 3, 2026.
Xu, L. et al., "Glucoraphanin: a broccoli sprout extract that ameliorates obesity-induced inflammation and insulin resistance," *Adipocyte*, 7.3 (2018): 218-225.

* cited by examiner

Glucoraphanin

Sulforaphane nitrile

Sulforaphane

Glucoerucin

Erucin

Erucin nitrile

METHODS FOR IMPROVING PHYSICAL EXERCISE PERFORMANCE

CROSS-REFERENCE TO RELATED APPLICATIONS

This application is a U.S. National Stage application under 35 U.S.C. § 371 of International Patent Application No. PCT/EP2021/085455, filed Dec. 13, 2021, which claims the benefit of Great Britain Patent Application No. 2019660.6, filed Dec. 14, 2020, the entirety of each of which are incorporated herein by reference.

The present invention relates to compositions, uses and methods for improving physical exercise performance, and/or improving adaptation to physical exercise, and/or modulating the concentration of lactate and/or glucose in the blood of a human subject.

It is well known that many individuals have a desire and/or need to improve physical exercise performance and/or improve adaptation to physical exercise. Such individuals range from athletes (at competitive, non-competitive, professional or non-professional levels), individuals who are generally interested in improving health and fitness, and individuals who desire and/or need the improvements for medical reasons.

Accordingly, there is a widespread demand for supplements that are able to improve physical exercise performance (e.g. for providing an enhancement in performance in a particular circumstance such as a competition) and/or improve adaptation to physical exercise (e.g. to aid a current training program or to achieve better results without the need to train as hard).

Such supplements are commercially important, which is reflected in the fact that there are currently a wide number of different supplements available on the market which are aimed at improving physical exercise performance and/or improving an individual's adaptation to physical exercise. These include antioxidants (such as vitamin C or coenzyme Q10); amino acids (particularly arginine, leucine, valine, glutamine, beta-alanine); caffeine; inorganic nitrate; ketone esters, bicarbonate, creatine; iron; herbal formulations; including ginseng, curcumin, and others.

Ketone ester supplementation has recently been shown to attenuate some negative effects, particularly the reduction in maximal heart rate and an increase in nocturnal adrenaline, during periods with very intense exercise (Poffe et al, 2019). However, supplementation with ketone esters induces mild acidosis which negates some of the positive effects. Furthermore, the scientific consensus on the performance enhancing effects of ketones are disputed.

Against this background, the present inventors have identified agents and compositions that can be used to significantly improve physical exercise performance and/or adaptation to physical exercise in human subjects. Surprisingly, the inventors' agents and compositions can be used to provide both a short-term enhancement of exercise performance, and a longer-term improvement in adaptation to physical exercise. Furthermore, unlike previously described supplements, the present invention modulates lactate concentrations in blood, attenuate hypoglycaemia and/or improve the adaptation to exercise training. This is novel to the compositions of the present inventors.

The inventors' findings therefore provide advantageous approaches to improve physical exercise in human individuals, for a range of medical, health and sporting applications.

In a first aspect, the invention provides a composition comprising sulforaphane, and/or glucoraphanin and/or myrosinase, for use in improving physical exercise performance and/or adaptation to physical exercise in a human subject.

In a second aspect, the invention provides a method for improving physical exercise performance and/or adaptation to physical exercise in a human subject, comprising the step of treating the human subject with a composition comprising sulforaphane, and/or glucoraphanin and/or myrosinase.

As described below and demonstrated in the accompanying Examples, the present inventors have surprisingly shown that administration of a composition comprising sulforaphane and/or glucoraphanin and/or myrosinase (such as a composition comprising broccoli sprouts, such as broccoli sprout juice) in human subjects can be used to improve physical exercise performance and/or adaptation to physical exercise.

In addition, the inventors have surprisingly found that administration of a composition comprising sulforaphane, and/or glucoraphanin and/or myrosinase (such as a composition comprising broccoli sprouts, such as broccoli sprout juice) in human subjects leads to changes in the blood lactate levels in human subjects. This is the first-time that the ability of such compositions to modulate lactate levels in human subjects has been shown.

In particular, two useful effects of modulating blood lactate in a human subject have been identified. Surprisingly, the dose-response curve for acute administration of such a composition is U-shaped, suggesting a biphasic effect of the composition on blood lactate levels. That finding has led the inventors to develop two particularly useful approaches for improving physical exercise performance.

The first is an "acute" effect, wherein a single dose of a composition of the invention results in a change in the blood lactate concentration that permits short-term control over blood lactate levels (and preferably, a short-term reduction in blood lactate levels), which may be particularly advantageous in increasing physical exercise performance.

The second surprising and useful effect of modulating blood lactate levels is that chronic administration of a composition of the invention results in a longer-term increase in blood lactate concentration, which may be particularly useful in applications for improving adaptation to physical exercise.

Links between blood lactate concentrations and physical exercise performance and/or physical exercise adaptation are known. It will therefore be appreciated that the inventors' development of new compositions for modulating blood lactate concentration has application in improving physical exercise performance and/or adaption to physical exercise in human subjects.

Furthermore, the inventors have surprisingly identified that a composition comprising sulforaphane, and/or glucoraphanin and/or myrosinase (such as a composition comprising broccoli sprouts, such as broccoli sprout juice) can be used to modulate (e.g. increase) the concentration of glucose in the blood in a human subject, and may therefore also be utilised to reduce the amount of time a subject spends in hypoglycaemia, particularly hypoglycaemia resulting from intense physical exercise.

Additionally, the inventors found that nrf2 was increased after consumption of compositions comprising sulforaphane and/or myrosinase and/or glucoraphanin (such as a composition comprising broccoli sprouts, such as broccoli sprout juice). Induction of nrf2 by the compositions in skeletal muscles of human subjects is a particularly novel and surprising finding of the inventors, and contributes towards the usefulness of the claimed invention.

By "physical exercise performance", we include the ability of a subject to carry out or execute a physical activity or exercise and may, for instance, include the speed, accuracy, duration, intensity at which exercise is carried out. Physical exercise performance can be measured in a variety of ways that are well known in the art, including for example by measuring levels of physical output, workload, maximal oxygen uptake, maximal effort, muscle fatigue, exhaustion, the ability to maintain normal blood glucose, lactic acidosis, the time to exhaustion at a constant workload and/or the time taken to complete a specific work, (e.g. to run, swim or cycle a specific distance).

Therefore, by "improving physical exercise performance" we include any improvement and/or increase in the ability of a subject to carry out or execute a physical activity or exercise, such as one or more of: an increased level of physical output; increased workload; increased maximal oxygen uptake; increased maximal effort; reduced exhaustion; reduced muscle fatigue; reduced hypoglycaemia; maintenance of normal blood glucose; reduced lactic acidosis; a decrease in the time to exhaustion at a constant workload and/or a decrease in the time taken to complete a specific work (e.g. to run, swim or bicycle a specific distance). Preferably, the subject can perform physical exercise with improved speed, accuracy, duration and/or intensity e.g. an athlete being able to run for a longer duration or at a higher intensity before exhaustion and/or muscle fatigue.

The improvement may be relative to the level of physical exercise performance had the subject not taken the composition. Alternatively the improvement may be relative to the physical exercise performance before the supplementation period and/or prior to receiving a composition according to the uses or methods of the invention.

By "supplementation period" we include the period or duration when the composition is administered. The supplementation period may depend on the type of administration. For example, for an acute dosage regime, the supplementation period may be a single day, but for a chronic or high dosage regime it may be over multiple days (e.g. 2 or more days).

The improvement in physical exercise performance may be a 1.01-fold, 1.02-fold, 1.03-fold, 1.04-fold, 1.05-fold, 1.06-fold, 1.07-fold, 1.09-fold, 1.1-fold, 1.2-fold, 1.25-fold, 1.3-fold, 1.4-fold, 1.5-fold, 1.6-fold, 1.7-fold, 1.8-fold, 1.9-fold, 2-fold, 2.25-fold, 2.5-fold, 3-fold, 4-fold or greater improvement, e.g. the fold change may be a reduction and/or increase in a relevant parameter that is indicative of improved physical exercise performance (including those listed herein).

The improvement may be an increase in the range of 1% to 100% improvement (such as a 5% to 100% improvement) in physical exercise performance, for example a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, 100% or greater improvement in physical exercise performance as determined by any relevant parameter.

The improvement in physical exercise performance may be an increase in the time taken to reach exhaustion during physical exercise. For example, the time taken to reach exhaustion may be increased by about 5 seconds, 10 seconds, 15 seconds, 20 seconds, 30 seconds, 40 seconds, 50 seconds, 70 seconds, 80 seconds, 90 seconds, 100 seconds, 110 seconds, 2 minutes, 3 minutes, 4 minutes, 5 minutes, 10 minute, 20 minutes, 30 minutes or greater.

The improvement to physical exercise performance may be an increase in power output and/or maximal power output. For example, the power output or maximal power output may increase by about 1 Watts, 2 Watts, 3 Watts, 4 Watts, 5 Watts, 6 Watts, 7 Watts, 8 Watts, 9 Watts, 10 Watts, 15 Watts, 20 Watts, 25 Watts, 30 Watts or greater.

The improvement to physical exercise performance may be achieved by reduced lactic acidosis, for example a 1%, 2%, 3%, 4%, 5%, 6%, 7%, 8%, 9%, 9.6%, 10%, 11%, 12%, 13%, 14%, 15%, 16%, 17%, 18%, 19%, 20%, 22% 25%, 30%, 40%, 50%, 60%, 70%, 80%, 90%, 100% or greater reduction in lactate levels in the human subject, optionally a 9.6%, 18% or 22% percent reduction in blood lactate concentration.

By "adaptation to physical exercise", we include changes or adjustments in a human subject, particularly physiological changes in a subject's body, that affect the ability of the subject to accommodate and/or adjust to the stress of physical exercise. As will be appreciated, adaptions to physical exercise may be positive adaptations (e.g. changes that improve the human subject's ability to accommodate the stress of physical exercise) or negative adaptations (e.g. changes that worsen the human subject's ability to accommodate the stress of physical exercise).

Therefore, by "improving adaptation to physical exercise", we include any changes that are beneficial and/or increase the ability of a human subject to adjust to and/or accommodate the stress of physical exercise.

The improved adaptation may be relative to the level of adaptation to physical exercise before the supplementation period and/or prior to receiving a composition according to the uses or methods of the invention. Alternatively, the improvement may be relative to the expected adaptation to physical exercise performance that would be expected had the subject not taken the composition.

An improved adaptation to physical exercise in the subject may be associated with one or more of the following physiological changes:

- maintained maximal heart rate;
- increased mitochondrial density;
- increased mitochondrial respiration;
- increased level of muscular lactate transport;
- reduced hypoglycaemia, including hypoglycaemia associated with intense physical exercise in the human subject;
- increased mitochondrial capacity (i.e. increased aerobic capacity);
- increased number and/or density and/or activity of mitochondria in cells of the human subject;
- increased number of capillaries in the body of the human subject, for example resulting from activation of mitochondrial biogenesis pathways;
- adapting to stress resulting from lactate levels;
- improved physical endurance of the human subject during physical exercise and/or improved tolerance to oxidative stress.

The improved adaptation to physical exercise may be a 1.01-fold, 1.02-fold, 1.03-fold, 1.04-fold, 1.05-fold, 1.06-fold, 1.07-fold, 1.09-fold, 1.1-fold, 1.2-fold, 1.25-fold, 1.3-fold, 1.4-fold, 1.5-fold, 1.6-fold, 1.7-fold, 1.8-fold, 1.9-fold, 2-fold, 2.25-fold, 2.5-fold, 3-fold, 4-fold or greater improvement, e.g. the fold change may be a reduction or increase in a relevant parameter that is indicative of improved adaptation to physical exercise.

The improved adaptation to physical exercise may be an improvement in the range of 1% to 100% (such as a 5% to 100% improvement), for example a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50%, 60%, 70%, 80%, 90%, 100% or greater improvement in adaptation and may be determined by any relevant marker or parameter indicative of improved adaptation (including those listed above).

For example, the improved adaptation to physical evidence may be an increase in mitochondrial respiration; for example the respiration (pmol) of $O_2$ per wet weight of muscle may increase by about 1 pmol, 2 pmol, 3 pmol, 4 pmol, 5 pmol, 6 pmol, 7 pmol. 8 pmol, 9 pmol, 10 pmol, 15, pmol, 20 pmol, 25 pmol, 30 pmol, 40 pmol, 50 pmol. 75 pmol, 100 pmol, 200 pmol or greater.

The improved in adaptation to physical exercise may be an increase in the maximal oxygen uptake or $VO_2$max. For example the increase in maximal oxygen uptake may be an increase by 0.05 l/min, 0.1 l/min, 0.15 l/min, 0.2 l/min, 0.25 l/min, 0.3 l/min, 0.35 l/min, 0.4 l/min, 0.45 l/min, 0.5 l/min or greater.

Sulforaphane (also known as sulphoraphane and 1-Isothiocyanato-4-(methanesulfinyl)butane) is a member of the isothiocyanate group of organosulphur compounds, and is found in many cruciferous vegetables, including broccoli.

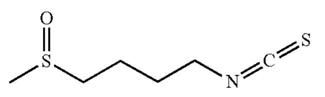

Sulforaphane (CAS number 4478-93-7)

Sulforaphane can be produced from conversion of glucoraphanin. Glucoraphanin (also known as glucorafanin and 4-Methylsulfinylbutyl glucosinolate) is a glucosinolate and may be found in a variety of sources, including in broccoli and cauliflower, particularly in the young sprouts.

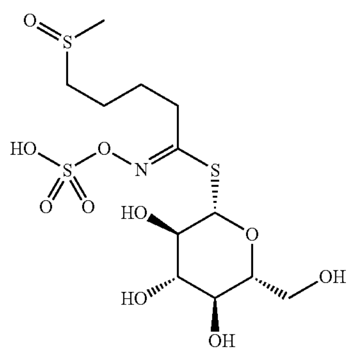

Glucoraphanin (CAS number 21414-41-5)

Glucoraphanin can be converted to sulforaphane, and this conversion may be assisted by the enzyme myrosinase. Myrosinase (also known as thioglucoside glucohydrolase, sinigrinase, and sinigrase) is a member of the glycoside hydrolase family and can catalyse the hydrolysis of glucosinolates, including glucoraphanin. The Enzyme Commission number of myrosinase is EC 3.2.1.147.

Figure 10:
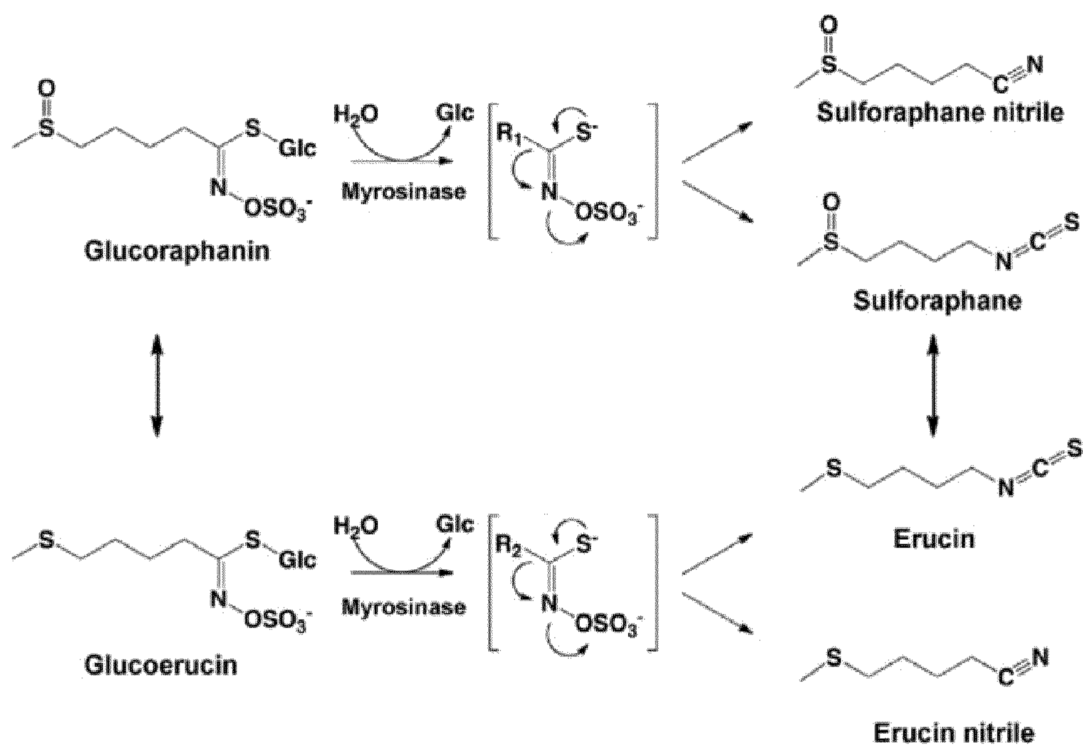

An overview of some conversions that lead to sulforaphane, including the enzymatic conversion by myrosinase, is shown in FIG. 10.

Broccoli sprouts, and sulforaphane, have been tested in clinical trials with the intention to reduce the development of cancer (Alumkal et al, 2015), reduce inflammatory markers in overweight individuals (Lopez-Chillon et al 2019), improve COPD and airway inflammation (Wise et al, 2016) and reduced symptoms of autism spectrum disorder (Singh et al, 2014) among others.

No studies have used broccoli sprouts or sulforaphane to improve physical exercise performance and/or to improve the adaptation to physical exercise in human subjects.

Sulforaphane has previously been injected into mice and shown to result in improved endurance, perhaps by counteracting oxidative stress-induced damage (Oh et al. 2017). It is very well known to those in the field that such mouse models cannot be used to predict the effect in human subjects. Accordingly, prior to the present inventors' findings, the effect of sulforaphane or human subjects was not known and could not be predicted. Whether sulforaphane would produce the same or a similar effect in human subjects, especially by oral administration, was completely unpredictable.

As is well known, mouse and/or rat models are often poor predictors of human reactions to exposure to a given compound and vice versa. It is common for a compound of interest to produce a given effect in a mouse model but have no (or very little) effect when tested in human subjects. There are a plethora of reasons why responses observed in mice cannot simply be extrapolated to humans, e.g. mice are genetically distinct, have different cellular molecule transporters, may have different expression of given enzymes that are relevant to the breakdown of a compound etc.

In fact, the unpredictability is evidenced by the fact that present inventors saw a significant effect on glucose levels in human subjects (see the accompanying Examples, study III), whereas in mice models sulforaphane exhibited no effect on glucose levels (Oh et al. 2017).

It is only the contribution by the present inventors which demonstrates that a composition comprising sulforaphane, and/or glucoraphanin and/or myrosinase (such as a composition comprising broccoli sprouts, such as broccoli sprout juice) may be utilised in human subjects for improving physical exercise performance and/or for improving adaptation to physical exercise. Furthermore, the specific effects on lactate levels, including the U-shaped dose response, were surprising to the inventors and was not be apparent from any previous mouse studies.

Furthermore, Oh et al. administered sulforaphane intraperitoneally to mice at doses of 25 mg/kg body weight. The same dose for an average 75 kg human corresponds to 1875 mg (16 mmol) of sulforaphane, which (considering that the conversion of glucoraphanin to sulforaphane is at best 40% (and more typically 15%), the amount of glucoraphanin needed would be 40 mmol, corresponding to 10 kg of broccoli sprouts) could not be feasibly administered. The present inventors have surprisingly found that significantly lower doses of sulforaphane, and/or glucoraphanin and/or myrosinase, elicit beneficial effects on physical exercise and/or blood lactate concentration and/or blood glucose in human subjects, and that they can be effectively administered to human subjects orally.

In one particularly preferred use or method of the invention, the human subject is administered a composition comprising sulforaphane. In another particularly preferred use or method of the invention, the human subject is administered a composition comprising glucoraphanin and/or myrosinase. In another particularly preferred use or method of the invention, the human subject is administered a composition comprising Broccoli sprouts (such as Broccoli sprout juice).

It will be appreciated by the skilled person that the administration of a composition of the invention may be by any suitable method that is known in art. This might include, but is not limited to oral administration, parenteral administration (including subcutaneous e.g. by injection or by depot tablet, intradermal, intrathecal, intramuscular e.g. by depot and intravenous), intra-peritoneal administration, transdermal administration, sublingual administration or rectal administration or injection. Furthermore, the compositions include those suitable for any such method of administration, including oral and parenteral (including subcutaneous e.g. by injection or by depot tablet, intradermal, intrathecal, intramuscular e.g. by depot and intravenous) administration.

The composition may be administered orally, buccally or sublingually in the form of tablets, capsules, ovules, elixirs, lozenges, chewing gums, solutions or suspensions, which may contain flavouring or colouring agents, for immediate-, delayed- or controlled-release applications.

Oral dosage forms may be solid, gel or liquid. The solid dosage forms may be tablets, capsules, granules, and/or bulk powders. Types of oral tablets may include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Dosage forms for rectal administration may include rectal suppositories, capsules and tablets. By "rectal suppositories" we include solid bodies for insertion into the rectum which melt or soften at body temperature releasing one or more biologically active ingredients. Pharmaceutically acceptable substances utilised in rectal suppositories may include bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories may include spermaceti and wax. Rectal suppositories may be prepared either by the compressed method or by moulding. The weight of a rectal suppository may be about 2 to 3 gm.

Tablets and capsules for rectal administration can be manufactured using the same pharmaceutically acceptable substance and by the same methods as for formulations for oral administration.

Transdermal administration may include administration via transdermal patches.

As discussed above, in an embodiment, the human subject is administered a composition comprising glucoraphanin, or glucoraphanin and myrosinase.

Glucoraphanin can be hydrolysed to the bioactive substance sulforaphane, in a process which is assisted by the enzyme myrosinase. If both myrosinase and glucoraphanin are administered in a composition, then there will be some conversion to sulforaphane.

Many plants containing high levels of glucoraphanin (e.g. broccoli and broccoli sprouts) also contain myrosinase, which is typically released when the plant is subjected to mechanical damage e.g. during food processing, damage by insects or microbial infection. It is believed that this process may be part of a natural defence mechanism of certain plant variety against pest insects or other animals that attack the plant during early development.

As well as being involved in the production of sulforaphane from glucoraphanin, myrosinase may also assist in the conversion of glucoraphanin to sulforaphane nitrile. Myrosinase is also able to assist the conversion of glucoerucin (also a glucosinolate present in cruciferous vegetables, including broccoli) to erucin or erucin nitrile. Furthermore, sulforaphane may be interconverted in vivo to erucin and vice versa (Clark et al. 2011).

It will be appreciated by the skilled person that any source of sulforaphane and/or glucoraphanin and/or myrosinase may be suitable to include in the compositions for the uses and methods according to the present invention.

For instance, the sulforaphane and/or glucoraphanin and/or myrosinase may be purified sulforaphane and/or purified glucoraphanin and/or purified myrosinase. The sulforaphane and/or glucoraphanin and/or myrosinase may be from a natural source of said compound(s) e.g. from a plant.

Sulforaphane and/or glucoraphanin and/or myrosinase can be found in a plethora of natural sources, including in cruciferous vegetables (also referred to as 'brassicas' or 'Cole crops').

Sources of sulforaphane and/or glucoraphanin and/or myrosinase may include any of the following: broccoli sprouts, mature broccoli, Brussels sprouts, kale sprouts, kale, cabbage sprouts, cabbage, cauliflower sprouts, cauliflower, broccoli raab sprouts, broccoli raab, red kale sprouts, red kale, kohlrabi sprouts, kohlrabi, red mizuna sprouts, red mizuna and/or in extracts thereof.

Myrosinase can be found in the following natural sources: brown mustard seeds; white mustard seeds; yellow mustard seeds; rocket (arugula or ruccola); rocket (arugula or ruccola) seeds; rocket (arugula or ruccola) sprouts; garden cress; garden cress seeds; garden cress sprouts; wasabi; wasabi seeds; wasabi sprouts; daikon; daikon seeds; daikon sprouts; horseradish; horseradish seeds; horseradish sprouts; radish; radish seeds; radish sprouts; and/or in extracts thereof.

In a preferred embodiment, the composition comprises: broccoli sprouts or an extract thereof; mature broccoli or an extract thereof; Brussels sprouts or an extract thereof; kale sprouts or an extract thereof; kale or an extract thereof; cabbage or an extract thereof; cabbage spouts or an extract thereof; cauliflower or an extract thereof; cauliflower sprouts or an extract thereof; broccoli raab or an extract thereof; broccoli raab sprouts or an extract thereof; red kale or an extract thereof; red kale sprouts or an extract thereof; kohlrabi or an extract thereof; kohlrabi sprouts or an extract thereof; red mizuna or an extract thereof; red mizuna sprouts or an extract thereof and/or optionally additionally comprises myrosinase.

By "sprouts" we include the shoots that emerge after a seed has germinated and before the plant has developed into a mature plant.

In particular, by "broccoli sprouts" we include the shoots that emerge after a broccoli seed has germinated and before the plant has developed into a mature broccoli plant. Typically, broccoli sprouts can be grown and harvested from seeds within 2 to 7 days.

In a third aspect, the invention provides a composition comprising broccoli sprout juice (which may be referred to herein as "BSJ"), for use in improving physical exercise performance and/or adaptation to physical exercise in a human subject. In a preferred embodiment the composition may further comprise brown mustard seeds.

In a fourth aspect, the invention provides a method for improving physical exercise performance and/or adaptation to physical exercise in a human subject, comprising the step of treating the human subject with a composition comprising broccoli sprout juice. In a preferred embodiment the composition may further comprise brown mustard seeds.

Furthermore, broccoli sprout juice may contain substances from the families isothiocyanates and/or glucosinolates, including sulforaphane nitriles and/or erucin and/or gluconapin.

In a further aspect, the invention provides a composition comprising isothiocyanates and/or glucosinolates (for example sulforaphane nitriles and/or erucin and/or gluconapin), for use in improving physical exercise performance and/or adaptation to physical exercise in a human subject.

In a further aspect, the invention provides a method for improving physical exercise performance and/or adaptation to physical exercise in a human subject, comprising the step of treating the human subject with a composition comprising isothiocyanates and/or glucosinolates (for example sulforaphane nitriles and/or erucin and/or gluconapin).

Preferably, the myrosinase is selected from: brown mustard seeds or an extract thereof; white mustard seeds or an extract thereof; yellow mustard seeds or an extract thereof; rocket or an extract thereof; rocket seeds or an extract thereof; rocket sprouts or an extract thereof; garden cress or an extract thereof; garden cress seeds or an extract thereof; garden cress sprouts or an extract thereof; wasabi or an extract thereof; wasabi seeds or an extract thereof; wasabi sprouts or an extract thereof; daikon or an extract thereof; daikon seeds or an extract thereof; daikon sprouts or an extract thereof; horseradish or an extract thereof; horseradish seeds or an extract thereof; horseradish sprouts or an extract thereof; radish or an extract thereof; radish seeds or an extract thereof; radish sprouts or an extract thereof; or purified or isolated myrosinase.

In a preferred embodiment, the composition comprises: brown mustard seeds or an extract thereof; white mustard seeds or an extract thereof; yellow mustard seeds or an extract thereof; rocket or an extract thereof; rocket seeds or an extract thereof; rocket sprouts or an extract thereof; garden cress or an extract thereof; garden cress seeds or an extract thereof; garden cress sprouts or an extract thereof; wasabi or an extract thereof; wasabi seeds or an extract thereof; wasabi sprouts or an extract thereof; daikon or an extract thereof; daikon seeds or an extract thereof; daikon sprouts or an extract thereof; horseradish or an extract thereof; horseradish seeds or an extract thereof; horseradish sprouts or an extract thereof; radish or an extract thereof; radish seeds or an extract thereof; radish sprouts or an extract thereof; or purified or isolated myrosinase The myrosinase may enhance the conversion of glucoraphanin to sulforaphane, optionally it may enhance the conversion relative to glucoraphanin in the absence of myrosinase.

The myrosinase may be provided in the form of a plant or an extract thereof containing both myrosinase and a large amount of inorganic nitrate.

Large amounts of inorganic nitrate may include inorganic nitrate at an amount of 25 mg or greater. For example, the large amount of inorganic nitrate may be in the range of 25 mg to 800 mg or greater. Preferably the amount of inorganic nitrate is 25 mg, 50 mg, 75 mg, 100 mg, 150 mg, 200 mg, 300 mg, 400 mg, 500 mg, 600 mg, 700 mg, or 800 mg.

It will be appreciated by the skilled person that any plant or extract thereof containing both myrosinase and a large amount of inorganic nitrate may be used. This includes rocket (arugula or ruccola); rocket (arugula or ruccola) seeds; rocket (arugula or ruccola) sprouts; garden cress; garden cress seeds; garden cress sprouts; radishes, radish seeds, radish sprouts and/or extracts thereof.

Nitrate in itself has exercise-enhancing properties which may be additive to those obtained by sulforaphane, and/or glucoraphanin and/or myrosinase, in the compositions for the uses and methods according to the present invention.

In a preferred embodiment, the invention provides a use or method composition comprising broccoli sprouts or an extract thereof and, optionally, mustard seeds or an extract thereof.

Preferably, the composition is for oral administration, and is administered orally to the human subject.

For example, the agent or active ingredient may be administered orally, buccally or sublingually in the form of tablets, capsules, ovules, elixirs, solutions or suspensions, which may contain flavouring or colouring agents, for immediate-, delayed- or controlled-release applications.

Oral dosage forms may be solid, gel or liquid. The solid dosage forms may be tablets, capsules, granules, and/or bulk powders. Types of oral tablets may include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

The oral administration may take the form of eating or drinking, particularly if the composition is comprised within a food, drink (e.g. a juice), a dietary supplement or any other appropriate form that would be appreciated by the skilled person.

The compositions may further comprise at least one pharmaceutically-acceptable or nutritionally-acceptable carrier, diluent or excipient material. The composition may be as a solid, gel or liquid formulation, and hence the at least one carrier may be a solid, gel or a liquid, optionally in combination with one or more additional solid, liquid or gel components.

Examples of a suitable liquid carrier include water, milk, coconut water, fruit drinks and juices, milk substitutes (soya drink, oat drink, nut and other plant-based drinks), sparkling beverages, oil formulations including one or more of a nut or vegetable oil, such as coconut, rapeseed, olive, palm, corn/maize; glycerin, propylene glycol; and aqueous solvents.

The carrier may be selected from a pharmaceutically acceptable carrier, excipient, or diluent; and a nutritionally acceptable i.e. food-grade carrier, excipient, or diluent material. For example, the carrier material may be a food.

Examples of suitable "pharmaceutically acceptable" carriers, excipients and diluents include those well known to a skilled person in the art, for example those given in Remington: The Science and Practice of Pharmacy, 19th ed., vol. 1 & 2 (ed. Gennaro, 1995, Mack Publishing Company).

By "nutritionally acceptable" or "food-grade" we include carriers, ingredients and excipients that meet the 'generally recognized as safe' (GRAS) criteria.

By "food" we include any substance for consumption to provide nutritional benefit or support for an organism. Examples of suitable food carriers include beverages (e.g. juices), dairy products (e.g. yoghurts, cheese, ice creams, infant formula and spreads such as margarine), dairy-alternative products (e.g. soy, nut or other plant-based drinks, yoghurts and spreads), cereal-based products (e.g. breads, biscuits, breakfast cereals, pasta and dry food bars such as health bars), and baby food (e.g. pureed fruit and/or vegetable).

Preferably, the formulation is a unit dosage containing a daily dose or unit, daily sub-dose or an appropriate fraction thereof, of the composition comprising the sulforaphane, and/or glucoraphanin and/or myrosinase, and/or broccoli sprout juice.

The composition may be a dietary supplement. By "dietary supplement" we include the meaning of a manufactured product intended to supplement the diet when taken by mouth, e.g. as a pill, capsule, tablet, or liquid. Dietary supplements may contain substances that are essential to life and/or those that have not been confirmed as being essential to life but may have a beneficial biological effect. When the composition according to the invention is in the form of a dietary supplement the carrier(s) to be added include those well known to a skilled person in the art, for example those given in Remington: *The Science and Practice of Pharmacy*, $19^{th}$ ed., vol. 1 & 2 (ed. Gennaro, 1995, Mack Publishing Company). Any other ingredients that are normally used in dietary supplements are known to a skilled person and may also be added conventionally together with the sulforaphane and/or glucoraphanin and/or myrosinase and/or broccoli sprout juice.

In an alternative embodiment, the composition comprises sulforaphane and is for intra-peritoneal, transdermal, sublingual or rectal administration or injection, and is administered intra-peritoneally, transdermally, sublingually, rectally or by injection to the human subject.

For example, dosage forms for rectal administration may include rectal suppositories, capsules and tablets. By "rectal suppositories" we include solid bodies for insertion into the rectum which melt or soften at body temperature releasing one or more biologically active ingredients. Pharmaceutically acceptable substances utilised in rectal suppositories may include bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories may include spermaceti and wax. Rectal suppositories may be prepared either by the compressed method or by moulding. The weight of a rectal suppository may be about 2 to 3 gm.

Tablets and capsules for rectal administration can be manufactured using the same pharmaceutically acceptable substance and by the same methods as for formulations for oral administration.

Transdermal administration may include administration via transdermal patches.

In a preferred embodiment, the composition modulates the concentration of lactate in the blood of the human subject.

Lactate is the ionic (electrically charged) form of and conjugate base of lactic acid. Lactate is produced during anaerobic glycolysis within muscles and is then transported in the blood to the liver where it can be converted to glucose. The glucose can be returned to the muscles and cyclically metabolised back to lactate in a process referred to as the lactic acid cycle (or Cori cycle).

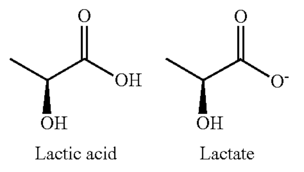

Lactic acid Lactate

By "modulate" we include exerting a modifying or controlling influence on the concentration of the lactate in the blood of the human subject. This may be an increase in the concentration of lactate in the blood. This may be a decrease in the concentration of lactate in the blood.

Normal blood lactate levels at rest are typically between 0.2-2.5 mM in a healthy subject. Normal blood lactate levels rise as exercise intensity increases, up to 8-25 mM after maximal exhaustive exercise.

Techniques for measuring blood lactate are well known in the art. For instance, blood lactate may be measured in blood from the capillaries of a punctured finger-tip and/or in blood drawn from an antecubital vein. The lactate may be measured using an enzymatic method e.g. via a Biosen C-line lactate analyser. Lactate may also be measured using colorimetric methods. Furthermore, lactate may also be measured in arterial blood, urine or sweat.

Lactic acid is produced when the body is low in oxygen or when the rate of carbohydrate oxidation is elevated and it needs to convert glucose or glycogen into energy. During intense exercise lactic acid is produced in a subject's muscles and accumulates. Lactic acid and/or the by-products of lactic acid production can lead to pain, sore muscles, cramps, lactic acidosis and muscle fatigue. Accordingly, a decrease in blood lactate levels may be beneficial in improving physical exercise performance in an individual, particularly on a short-term or one-off basis.

A lower blood lactate concentration during submaximal work or exercise is a classic positive adaptation to a period of exercise training indicative of enhanced mitochondrial oxidation of pyruvate. Typically, decreases in blood lactate levels may be observed in individuals after several weeks of endurance training (Mayes et al. 1987) and are expected to be associated with an improved physical performance.

The uses and/or methods of the present invention may comprise an acute or single administration regime. By "acute or single administration regime" we include that the composition is administered once and in a single dose. Alternatively, the uses and/or methods of the present invention may comprise a long-term or chronic administration regime. By "long-term or chronic administration regime" we include that the composition is administered for a period of at least two days.

As discussed herein and shown in the accompanying Examples, the inventors identified two key effects of compositions of the invention on blood lactate levels. Surprisingly, the dose-response curve is a U-shaped curve—certain doses result in a reduction of blood lactate levels, while higher doses cause an increase in blood lactate levels. This distinct U-shaped dose response curve suggests there is a biphasic effect of BSJ on blood lactate levels, which may be used to modulate blood lactate levels in a human subject.

Firstly, the inventors have found that acute administration of broccoli sprout juice (BSJ) in human subjects results in an acute effect on blood lactate concentration after submaximal exercise.

Secondly, the inventors have found that chronic administration of broccoli sprout juice (BSJ) can used to modulate blood lactate levels. In particular, administration of the compositions in subjects who had not undertaken exercise training resulting in increased lactate levels during submaximal exercise. However, the maximal attainable workload was unchanged, thereby indicating that positive adaptations to the increased lactate levels had occurred in those subjects.

Furthermore, administration of the compositions in subjects who were undertaking exercise training during the supplementation period, resulted in significantly decreased lactate levels and subjects' ability to adapt to the workload was enhanced.

Based on the disclosure and teaching herein, the skilled person would appreciate that the dosage (e.g. amount of sulforaphane, glucoraphanin, myrosinase, broccoli sprout juice, isothiocyanates and/or glucosinolates) and/or the administration regime (e.g. acute single administration or chronic administration over multiple days) may be adjusted in order to achieve the desired effect on blood lactate levels and ultimately result in improved physical exercise performance and/or improved adaptation to physical exercise.

As well as having applications in improving physical exercise performance and/or improving adaptation to physical exercise, the ability to modulate blood lactate levels has other benefits. It will be appreciated by the skilled person that modulation of blood lactate levels can be utilised in the treatment and/or prevention of medical conditions associated with increased or decreased lactate levels, lactic acidosis and/or fatigue.

By "treatment" we include the effect of reversing, reducing, alleviating, ameliorating, arresting or curing the symptoms, clinical signs and/or underlying pathology of a specific disorder, disease, injury or condition in manner to improve or stabilise a subject's condition.

The term "prevention" is art-recognised, and when used in relation to a condition, it includes reducing the frequency of, and/or delaying the onset of symptoms, clinical signs, and/or underlying pathology of a specific disorder, disease, injury or medical condition in a human subject relative to a human subject who does not receive the agent. The term "prevention" includes prophylactic treatment. The term "prophylactic treatment" is art-recognised and includes administration of a composition prior to clinical manifestation of the unwanted condition, such that it fully or partially protects the human subject against developing the unwanted condition; if it is administered after manifestation of the unwanted condition, the treatment is therapeutic (i.e. it is intended to diminish, ameliorate, or stabilise the existing unwanted condition or side effects thereof).

The following conditions are associated with an increase in lactate levels:

- thiamine deficiency (especially during TPN);
- impaired delivery of oxygen to cells in tissues (e.g. from impaired blood flow (hypoperfusion));
- bleeding;
- polymyositis;
- ethanol toxicity;
- shock;
- advanced liver disease;
- diabetic ketosis;
- excessive exercise (overtraining);
- regional hypoperfusion (e.g. bowel ischemia or marked cellulitis);
- cancers such as Non-Hodgkin's and Burkitt lymphomas;
- pheochromocytoma;
- tumour lysis syndrome.

It will be apparent to the skilled person that utilising the compositions of the uses and/or methods of the invention to modulate lactate levels in a way that decreases blood lactate may be beneficial in human subjects with one of more of these conditions e.g. in the treatment and/or prevention of one or more of such condition(s).

The following conditions are associated with a decrease in lactate levels:

- McArdle's disease;
- LDH-deficiency;
- Fructose 1,6-bisphosphatase deficiency;
- Glucose-6-phosphatase deficiency;
- GRACILE syndrome;
- pyruvate dehydrogenase deficiency;
- pyruvate carboxylase deficiency;
- Leigh syndrome.

It will be apparent to the skilled person that utilising the compositions of the uses and/or methods of the invention to modulate lactate levels in a way that increases blood lactate may be beneficial in human subjects with one or more of these condition(s) e.g. in the treatment and/or prevention of one or more of such condition(s).

The administration of the following drugs is associated with increased lactate levels:

- Metformin;
- Acetaminophen;
- Linezolid;
- Isoniazid;
- Propofol;
- Epinephrine;
- Propylene glycol;
- Nucleoside reverse-transcriptase inhibitors (for example Abacavir/dolutegravir/lamivudine); Emtricitabine/tenofovir;
- Potassium cyanide (cyanide poisoning);
- Fialuridine.

It will be apparent to the skilled person that utilising the compositions of the uses and/or methods of the invention to modulate lactate levels in a way that decreases blood lactate may be beneficial in human subjects taking these drugs e.g. in the alleviation of side effects resulting from lactate levels.

Preferably, the composition modulates the concentration of glucose in the blood of the human subject. Even more preferably, the composition increases the concentration of glucose in the blood of the human subject.

Glucose is a simple sugar and a monosaccharide having the molecular formula $C_5H_{12}O_6$. It is an important source of energy in energy metabolism. Methods for determining the concentration of glucose in the blood are well-known in art; for example finger prick tests using a flash glucose monitor or a continuous glucose monitor.

By "modulate" we include exerting a modifying or controlling influence on the concentration of the glucose in the blood of the human subject. This may be an increase in the concentration of glucose in the blood. This may be a decrease in the concentration of glucose in the blood. Preferably, this is an increase in the concentration of glucose in the blood.

The increase or decrease in the concentration of glucose in the blood may be relative to the normal blood glucose concentration in the human subject. Typically, a blood glucose level between 4 to 8 mM is considered normal. The increase or decrease in the concentration of glucose in the blood may be relative to the concentration of glucose in the blood of the human subject before the supplementation period and/or prior to receiving a composition according to the uses or methods of the invention.

The uses and/or methods of the present invention may be utilised in acute or single administration regime. By "acute or single administration regime" we include that the composition is administered once and in a single dose.

In a preferred embodiment of the invention, the composition is administered once and in a single dose.

In a preferred embodiment, the human subject is in need, or is desirous, of improved physical exercise performance.

It will be appreciated that a human subject in need of improved physical exercise performance may be suffering from poor or inadequate physical exercise performance, for example in relation to their particular training requirements. A human subject in need of improved physical exercise performance may be suffering from exhaustion, muscle fatigue and/or lactic acidosis. A human subject in need of improved physical exercise performance may be about to undertake physical exertion, especially in an athletic event or competition.

It will be appreciated that a human subject desirous of improved physical exercise performance may want or wish to better their physical exercise performance. A human subject desirous of improved physical exercise performance may not be suffering from poor or inadequate physical exercise performance, but may wish to increase or boost their physical exercise performance relative to their normal state. A human subject in need of improved physical exercise performance may be about to undertake physical exertion, especially in an athletic event or competition.

In a preferred embodiment, the composition comprises between 1 g and 140 g of broccoli sprouts; for example the composition comprises 10 g, 25 g, 50 g, 60 g, 70 g, 80 g, 90 g, 100 g, 110 g, 120 g, 130 g or 140 g of broccoli sprouts.

In a preferred embodiment, the composition comprises between 0.0055 mg and 500 mg of glucoraphanin (e.g. between 1.75 mg and 500 mg of glucoraphanin); for example 0.0055 mg, 0.01 mg, 0.025 mg, 0.05 mg, 0.075 mg, 0.1 mg, 0.25 mg, 0.5 mg, 0.75 mg, 1 mg, 1.75 mg, 17.5 mg, 43.75 mg, 87.5 mg, 105 mg, 122.5 mg, 131.25 mg, 140 mg, 157.5 mg, 175 mg, 192.5 mg, 210 mg, 227.5 mg, 245 mg, 300 mg, 400 mg or 500 mg. Methods for measuring glucoraphanin in a sample are well known in the art. For example, glucoraphanin can be measured using the method described in Abukhabta et al. 2020.

The compositions for the uses and/or methods of the present invention may comprise glucoraphanin at an amount between 0.13 and 1150 μmol (e.g. an amount between 4 and 1150 μmol); for example 0.13 μmol, 0.25 μmol, 0.5 μmol, 0.75 μmol, 1 μmol, 2 μmol, 3 μmol, 4 μmol, 40 μmol, 100 μmol, 200 μmol, 240 μmol, 280 μmol, 320 μmol, 360 μmol, 400 μmol, 440 μmol, 480 μmol, 520 μmol, 560 μmol, 600 μmol, 700 μmol, 800 μmol, 900 μmol, 1000 μmol, 1100 μmol or 1150 μmol.

In a preferred embodiment the composition comprises between 5.9 μg and 100 mg of sulforaphane (e.g. between 0.18768 mg and 100 mg of sulforaphane); for example 5.9 μg, 10 μg, 25 μg, 50 μg, 75 μg, 0.1 mg, 0.15 mg, 0.188 mg, 1.188 mg, 4.962 mg, 9.384 mg, 11.261 mg, 13.138 mg, 15.014 mg, 16.891 mg, 18.768 mg, 20.6448 mg, 22.5216 mg, 24.3984 mg, 26.2752 mg, 30 mg, 40 mg, 50 mg, 60 mg, 70 mg, 80 mg, 90 mg or 100 mg. Methods for measuring sulforaphane in a sample are well known in the art. For example, sulforaphane can be measured using the method described in Abukhabta et al. 2020.

In an embodiment, the composition for the uses and/or methods of the invention may comprise sulforaphane at an amount between 50 nmol and 850 μmol (e.g. between 1.6 and 850 μmol); for example 50 nmol, 100 nmol, 250 nmol, 500 nmol, 750 nmol, 1 μmol, 1.25 μmol, 1.5 μmol, 1.6 μmol, 16 μmol, 40 μmol, 80 μmol, 96 μmol, 112 μmol, 128 μmol, 144 μmol, 160 μmol, 176 μmol, 192 μmol, 208 μmol, 224 μmol, 250 μmol, 350 μmol, 450 μmol, 550 μmol, 650 μmol, 750 μmol or 850 μmol.

In a preferred embodiment, the composition comprises between 0.5 g and 10 g of mustard seeds, for example 0.5 g, 0.75 g, 1 g, 1.5 g, 2 g, 3 g, 4 g, 5 g, 6 g, 7 g, 8 g, 9 g, 10 g of mustard seeds; optionally wherein the mustard seeds are brown mustard seeds.

In an embodiment, the composition for the uses and/or methods of the present invention may comprise between 0.25 and 40 units of myrosinase, for example between 0.25 and 2 units; 0.5 and 4 units; 1 and 8 units; 1.5 and 12 units; 2 and 16 units; 2.5 and 20 units; 3 and 24 units; 3.5 and 28 units; 4 and 32 units; 4.5 and 36 units; or 5 and 40 units. Methods for measuring myrosinase in a sample are well known in the art. For example, myrosinase can be measured using the method described in Wilkinson et al. 1984.

In a preferred embodiment, the composition reduces the concentration of lactate in the blood of the human subject.

The reduction in the concentration of lactate in the blood may be relative to the normal blood lactate concentration in the human subject. The reduction in the concentration of lactate in the blood may be relative to the concentration of lactate in the blood of the human subject before the supplementation period and/or prior to receiving a composition according to the uses and/or methods of the invention.

Normal blood lactate levels at rest are typically between 0.2-2.5 mM in a healthy subject. Normal blood lactate levels rise as exercise intensity increases, up to 8-25 mM after maximal exhaustive exercise.

The uses and methods of the present invention may result in a reduction in blood lactate levels at exercise intensities between the range of 10 to 95% maximal oxygen consumption.

The uses and methods described herein may result in a reduction in blood lactate levels at submaximal exercise intensities; for example at an average exercise intensity of 65% of maximal oxygen consumption or 80% of maximal oxygen consumption.

The reduction in the concentration of lactate in the blood of the human subject may be in the range of 10% to 25%; for example it may be 10%, 18%, 22% or 25%.

In a preferred embodiment, the composition for the uses and/or methods of the invention is administered to the human subject before physical exercise, and preferably: less than six hours before; or less than five hours before; or less than three hours before; or less than two hours before; or less than one hour before physical exercise.

In another embodiment, the composition for the uses and/or methods of the invention is administered to the human subject after physical exercise. Preferably, the composition is administered less than three hours after exercise, less than two hours after exercise or less than one hour after exercise. The composition of the invention may be used in recovery from exercise by aiding the elimination of lactate that has built up after intense exercise.

In an embodiment, the composition improves physical exercise performance in the human subject.

In a preferred embodiment, the composition improves the ability of the human subject to endure oxidative stress resulting from physical exercise.

By "oxidative stress" we include an imbalance between the free radicals and the ability of cells and/or the body to counteract or detoxify the reactive intermediates, e.g. via antioxidants. Free radicals are oxygen containing molecules comprising one or more unpaired electron, making them highly reactive. Antioxidants are compounds that can donate an electron to a free radical without becoming destabilised.

In a preferred embodiment, the composition improves the physical endurance of the human subject during physical exercise.

By "physical endurance" we include the ability of the human subject to exert themself or exercise for long period of time. Physical endurance includes the ability to resist, withstand or recover from fatigue during physical exercise.

In a preferred embodiment, the human subject is suffering from lactic acidosis.

By "lactic acidosis" we include the build-up of lactate (especially L-lactate) in the body, which results in a lowered pH in the blood stream. The excessive acid may accumulate in the blood due to an overproduction or an underutilisation of lactic acid.

In a preferred embodiment, the composition is used in the prevention or treatment of a medical condition associated with increased lactic acidosis and/or fatigue, for example one or more of the following: mitochondrial myopathies (MELAS syndrome), biotin deficiency, bacterial infection in the bloodstream or body tissues (sepsis), glycogen storage diseases, Reye syndrome, short-bowel syndrome, liver failure, hypoxia (for example hypoxia caused by a defect in the heart or blood vessels), bacterial meningitis, thiamine deficiency (especially during TPN), impaired delivery of oxygen to cells in tissues (e.g. from impaired blood flow (hypoperfusion)), bleeding, polymyositis, ethanol toxicity, shock, advanced liver disease, diabetic ketosis, excessive exercise (overtraining), regional hypoperfusion (e.g. bowel ischemia or marked cellulitis), cancers such as Non-Hodgkin's and Burkitt lymphomas, pheochromocytoma, and/or tumour lysis syndrome.

In a preferred embodiment, the composition is used to reduce lactic acidosis caused by metformin or acetaminophen.

In a preferred embodiment, the composition is used to reduce increased blood lactate levels caused by Linezolid, Isoniazid, Propofol, Epinephrine, Propylene glycol, Nucleoside reverse-transcriptase inhibitors (for example Abacavir/dolutegravir/lamivudine), Emtricitabine/tenofovir, Potassium cyanide (cyanide poisoning) and/or Fialuridine.

The uses and methods of the invention may be used to modulate lactate levels and accordingly may be used in the treatment and/or prevention of conditions associated with changes in lactate levels, for example conditions associated with an increase in lactate levels; and/or conditions associated with a decrease in lactate levels.

The uses and/or methods of the present invention may be utilised in long-term or chronic administration regime. By "long-term or chronic administration regime" we include that the composition is administered for a period of at least two days.

In a preferred embodiment, the composition is administered daily, for a period of at least two days; preferably for a period of three days, or four days, or five days, or six days, or seven days, or two weeks, or three weeks, or four weeks, or one month, or two months, or three months, or four months, or five months, or six months, or one year, or more.

By "daily" we include at least once every day. For example, the composition may be administered once a day, twice a day, three times a day or at least once within a given window within a day (e.g. twice within a 16-hour window per day).

In a preferred embodiment, the human subject is in need, or is desirous, of improved adaptation to physical exercise and/or improved physical exercise performance.

It will be appreciated that a human subject in need of improved adaptation to physical exercise may be suffering from poor or inadequate adaption to physical exercise, for example in relation to their particular training requirements. A human subject in need of adaptation to physical exercise may be suffering from inadequate muscle lactate transport, inadequate mitochondrial number, respiration, density and/or activity, inadequate tolerance to oxidative stress during exercise and/or inadequate physical endurance. A human subject in need of improved adaptation to physical exercise may be planning to participate in physical exertion, for example be planning to participate in an athletic event or competition.

It will be appreciated that a human subject desirous of improved adaptation to physical exercise may want or wish to better their adaptation to physical exercise. A human subject desirous of improved adaptation to physical exercise may not be suffering from poor or inadequate adaptation to physical exercise, but may wish to increase or boost their adaptation to physical exercise relative to their normal state. A human subject in need of improved adaptation to physical exercise may be planning to undertake physical exertion, especially an athletic event or competition.

In an embodiment, the composition comprises more than 120 g of broccoli sprouts; preferably more than 150 g of broccoli sprouts; for example 200 g of broccoli sprouts.

In a preferred embodiment, the total amount of broccoli sprouts consumed within a 16-hour period of each day is between 120 g and 200 g, preferably 150 g and 200 g; for example wherein the human subject consumes two doses of 75 g of broccoli sprouts within a 16-hour period of each day.

In a preferred embodiment, the composition increases the concentration of lactate in the blood of the human subject; optionally by at least 10%, at least 15%, at least 20%, or at least 24%, compared to the normal blood lactate concentration in the human subject.

The increase in the concentration of lactate in the blood may be relative to the normal blood lactate concentration in the human subject. The increase in the concentration of lactate in the blood may be relative to the concentration of lactate in the blood of the human subject before the supplementation period and/or prior to receiving a composition according to the uses and/or methods of the invention.

Normal blood lactate levels at rest are typically between 0.2-2.5 mM in a healthy subject. Normal blood lactate levels rise as exercise intensity increases, up to 8-25 mM after maximal exhaustive exercise.

In a preferred embodiment, the composition results in an increase in blood glucose in the human subject.

In a preferred embodiment, the composition reduces the amount of time the human subject spends in hypoglycaemia.

By "hypoglycaemia" we include circumstances where the blood sugar levels have fallen to below the normal level for a human subject. Hypoglycaemia is often associated with intense physical exercise in the human subject. Normoglycemia (normal blood sugar levels) are considered to be between 4 to 8 mM glucose. Hypoglycaemia is considered to be a blood sugar level of less than 4 mM.

In a preferred embodiment, the composition reduces hypoglycaemia associated with intense physical exercise in the human subject.

By "intense physical exercise" we include high-intensity exercise and/or exercise that leads to a human subject experience on or more of the following: a heart rate of at least 70% of the human subjects maximum heart rate; deep and rapid breathing; being unable to say more than a few words without pausing for breath; moderate or heavy sweating; and/or exhaustion.

By "reduced hypoglycaemia" we include a reduction in the amount of time the human subject spends in hypoglycaemia.

In a preferred embodiment, the composition improves adaptation to physical exercise in the human subject.

Preferably, the improved adaptation to physical exercise comprises:

increased number and/or density and/or activity of mitochondria in cells of the human subject; and/or increased number of capillaries in the body of the human subject, for example resulting from activation of mitochondrial biogenesis pathways.

By "mitochondrial density" (also known as mitochondrial volume density) we include the percentage of muscle fibre volume occupied by mitochondria in the human subject and/or the number of mitochondria per unit weight of muscle. The size and/or number of mitochondria will have an effect on the mitochondrial density. An increased mitochondrial density can lead to increased energy availability for muscles and can result in an individual being able to train or compete faster or for longer.

By "mitochondrial biogenesis" we include the process by which cells increase their mitochondrial mass and/or the growth and division of pre-existing mitochondria.

By "mitochondrial capacity" we include the metabolic capacity and the respiratory capacity of the mitochondria.

Methods of measuring mitochondrial density, biogenesis and/or capacity are well known in the art. For example, mitochondrial density can be measured by determining the activity of citrate synthase (a mitochondrial enzyme) and relating it to the weight of the muscle (Larsen et al. 2012).

Mitochondrial biogenesis may be assessed with PCR-methodology by measuring the amount of mRNA of the POC-1alpha, the master regulator of mitochondrial biogenesis (Sunderland et al. 2009). Mitochondrial capacity may be measured by assessing the mitochondrial respiratory capacity in saponin-permeabilized muscle fibres (Cardinale et al. 2018)

In a preferred embodiment, the composition improves the physical endurance of the human subject during physical exercise and/or improves tolerance to oxidative stress.

In a preferred embodiment, the improved adaptation to physical exercise results from the body of the human subject adapting to stress resulting from lactate levels.

In a preferred embodiment, after administration for a period of at least two days, physical exercise performance is improved in the human subject.

In a preferred embodiment, the composition is administered to a subject who undertakes exercise training during the administration period, optionally who undertakes high-intensity training during part or all of the supplementation period, e.g. at >90% maximal oxygen consumption. Preferably, the composition results in an increase in blood lactate in the subject.

In an alternative preferred embodiment, the composition is administered to subject who does not participate in any exercise training during the administration period and/or maintains their normal lifestyle. Preferably, the composition results in a decrease in blood lactate in the subject.

In a preferred embodiment, the composition is used in the prevention or treatment of McArdle's disease, LDH-deficiency, Fructose 1,6-bisphosphatase deficiency, Glucose-6-phosphatase deficiency, GRACILE syndrome, pyruvate dehydrogenase deficiency, pyruvate carboxylase deficiency and/or Leigh syndrome.

In an embodiment, the human subject is male or is female.

In a preferred embodiment, the human subject is an athlete. By "athlete" we include the meaning that, on average, the person does at least five hours of vigorous exercise per week and/or a human that competes against other humans in one or more sporting event(s) (e.g. occasionally or regularly).

In a preferred embodiment, the human subject is desirous, and/or in need, of improved athletic performance.

It will be appreciated that a human subject in need of improved athletic performance may be suffering from poor or inadequate athletic performance e.g. if they are a professional athlete they may be performing below expectations. A human subject in need of improved athletic performance may be suffering from exhaustion, muscle fatigue and/or lactic acidosis. A human subject in need of improved athletic performance may be about to undertake physical exertion, especially in an athletic event or competition.

It will be appreciated that a human subject desirous of improved athletic performance may want or wish to better their athletic performance. A human subject desirous of improved athletic performance may not be suffering from poor or inadequate athletic performance, but may wish to increase or boost their athletic performance relative to their normal state. A human subject in need of improved athletic performance may be about to undertake physical exertion, especially in an athletic event or competition.

Preferably, improved physical exercise performance in the human subject comprises one or more of: increased physical output; increased workload; increased maximal oxygen uptake, increased maximal effort; reduced exhaustion; reduced muscle fatigue; reduced hypoglycaemia, maintenance of normal blood glucose, reduced lactic acidosis, a decrease in the time to exhaustion at a constant workload and/or a decrease in the time taken to complete a specific work (e.g. to run, swim or cycle a specific distance).

By "physical output" we include the power output in watts during exercise. Maximal power output may be determined by human subjects performing an incremental exercise protocol to exhaustion.

By "workload" we include the amount of work a human subject performs. Workload may be combination of the volume and intensity of the exercise. Maximum workload may be equivalent to the maximum work capacity in watts that a human subject can undertake.

Effort in an exercise context accounts for the intensity and duration of exertion. By "maximal effort" we include the maximum intensity and duration of exertion the human subject can tolerate.

By "exhaustion" we include extreme physical or mental fatigue and/or the inability to continue physical exercise at a given intensity. Exhaustion may occur when the muscles in a human subject use up their energy stores and stop working or become fatigued. Exhaustion can be measured by assessing the time taken to reach exhaustion during a given physical exercise protocol, particularly an incremental physical exercise protocol.

Reduced exhaustion may be indicated by an increase in the time taken to reach exhaustion during a physical exercise protocol (for example an incremental physical exercise protocol) relative to the time taken to reach exhausting during the same exercise protocol prior to receiving a composition according to the uses or methods of the invention.

By "muscle fatigue" we include the decline in ability of a muscle to generate force and/or perform over time. Muscle fatigue results in a decrease in maximal force or power produced in response to contractile activity. It may occur via neural fatigue and/or metabolic fatigue, wherein metabolic fatigue normally results from a shortage of fuel (substrates such as adenosine triphosphate (ATP) or glycogen) in the muscle fibre or an accumulation of substances (metabolites) within the muscle fibre that interfere with $Ca^{2+}$ signalling. Such metabolites may include chloride, potassium ions and/or lactic acid.

Preferably, improving adaptation to physical exercise in the human subject comprises one or more of: maintained maximal heart rate; increased mitochondrial density; increased mitochondrial respiration; increased level of muscular lactate transport; and/or reduced hypoglycaemia.

By "maximal heart rate" (also known as HRmax) we include the highest heart rate a human subject can achieve without severe problems through exercise stress and/or the fastest rate at which the human subject's heart will beat in one minute. Maximal heart rate can be determined by methods that are standard in the art, for example via a cardiac stress test. Maximal heart rate is measured in beats per minute (bpm) and may be affected by a plethora of factors, including for example age, physical fitness and stress.

By "mitochondrial respiration" we include the metabolic processes that take place in mitochondria to convert the energy stored in macronutrients, such as sugar, to adenosine triphosphate (ATP), which is the universal energy donor in cells.

By "muscular lactate transport" we include the transport of lactate produced by glycolysis from the muscle to the blood and/or liver.

In a preferred embodiment, the composition comprises broccoli sprouts (or an extract thereof) and/or mustard seeds (or an extract thereof), wherein the composition has a broccoli sprout (or extract thereof) to mustard seed (or extract thereof) ratio between 100:0 to 1:10; for example a broccoli sprout (or extract thereof) to mustard seed (or extract thereof) ratio of 100:1.

The ratio may be expressed in terms of weight, for example a broccoli sprout to mustard seed ratio of 100:1 would include of 100 grams of broccoli sprouts to 1 gram of mustard seeds, 50 grams of broccoli to 0.5 grams of mustard seeds, and so on.

It will be appreciated that any of extracts referred to herein may be prepared by any conventional method in the art. The extracts may be freeze dried. Freeze-drying may stabilise any sulforaphane and/or glucoraphanin present in the extract.

In a preferred embodiment, the composition comprises 50 g of broccoli sprouts (or an extract thereof) and 0.5 g mustard seeds (or an extract thereof). In another preferred embodiment, the composition comprises 50 g of broccoli sprouts (or an extract thereof).

In an embodiment, the composition is administered between two and ten times per day.

In an embodiment, the composition is made by homogenising, blending, pureeing, shredding, cutting and/or chopping broccoli sprouts optionally with water, thereby forming a juice. The composition may subsequently immediately frozen, e.g. to −80° C. The composition may be thawed prior to consumption and/or administration. After thawing, 1% based on weight (0.75 grams mustard seed in 75 g of broccoli sprouts) of myrosinase containing powdered brown mustard seeds may be added to the juice.

In a further aspect, the invention provides sulforaphane for use, or glucoraphanin and/or myrosinase for use, or broccoli sprouts for use, in modulating the concentration of lactate and/or glucose in the blood of a human subject. In a preferred aspect, the invention provides sulforaphane for use, or glucoraphanin and/or myrosinase for use, or broccoli sprouts for use, in modulating the concentration of lactate and/or increasing the concentration of glucose in the blood of a human subject.

In a further aspect, the invention provides a method for modulating the concentration of lactate and/or glucose in the blood of a human subject, comprising the step of treating the human subject with sulforaphane, or with glucoraphanin and/or myrosinase, or broccoli sprouts. In a preferred aspect, the invention provides a method for modulating the concentration of lactate and/or increasing the concentration of glucose in the blood of a human subject, comprising the step of treating the human subject with sulforaphane, or with glucoraphanin and/or myrosinase, or broccoli sprouts.

In a further aspect, the invention provides the use of sulforaphane, or glucoraphanin and/or myrosinase, or broccoli sprouts, in the manufacture of a medicament for improving physical exercise performance and/or adaptation to physical exercise in a human subject.

In a further aspect, the invention provides the use of sulforaphane, or glucoraphanin and/or myrosinase, or broccoli sprouts, in the manufacture of a medicament for modulating the concentration of lactate and/or glucose in the blood of a human subject. In a preferred aspect, the invention provides the use of sulforaphane, or glucoraphanin and/or myrosinase, or broccoli sprouts, in the manufacture of a medicament for modulating the concentration of lactate and/or increasing the concentration of glucose in the blood of a human subject.

The invention will now be described by reference to the following Figures and Examples.

LIST OF FIGURES

FIG. 1: Effect of acute administration of BSJ on blood lactate concentration after submaximal exercise.

Figure 2:
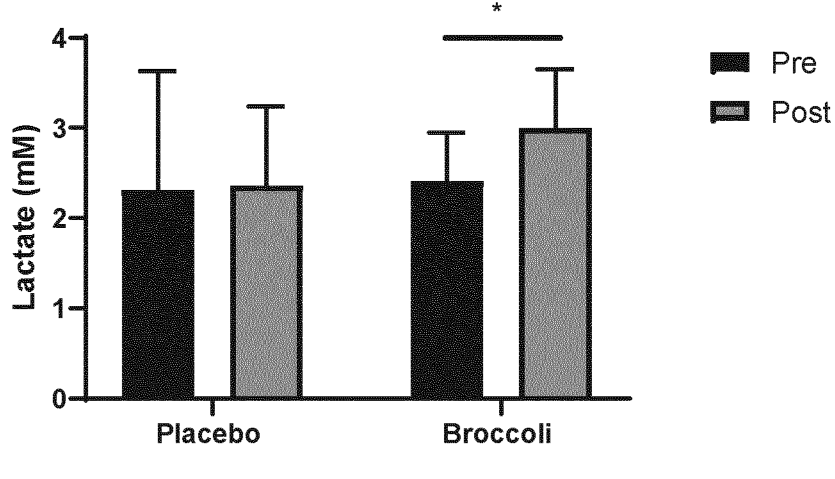

FIG. 2: Effect of chronic administration of BSJ on blood lactate levels at submaximal exercise.

Figure 3:
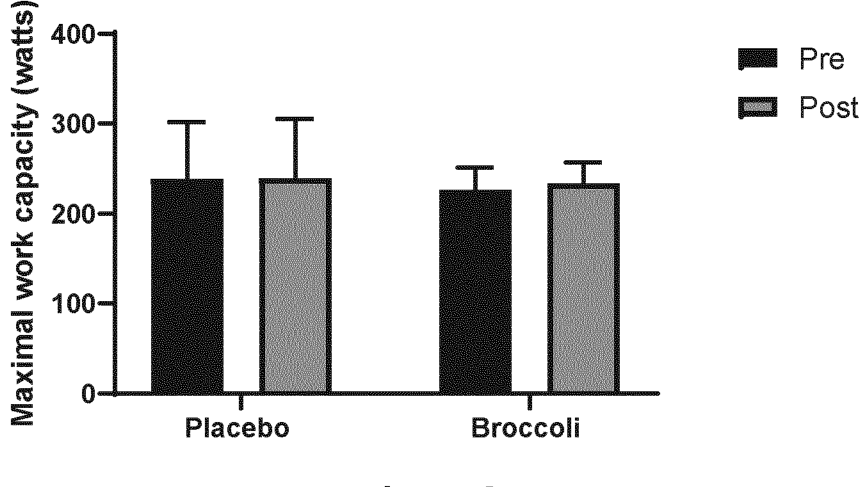

FIG. 3: Effect of chronic administration of BSJ on maximal attainable workload during incremental exercise.

Figure 4:
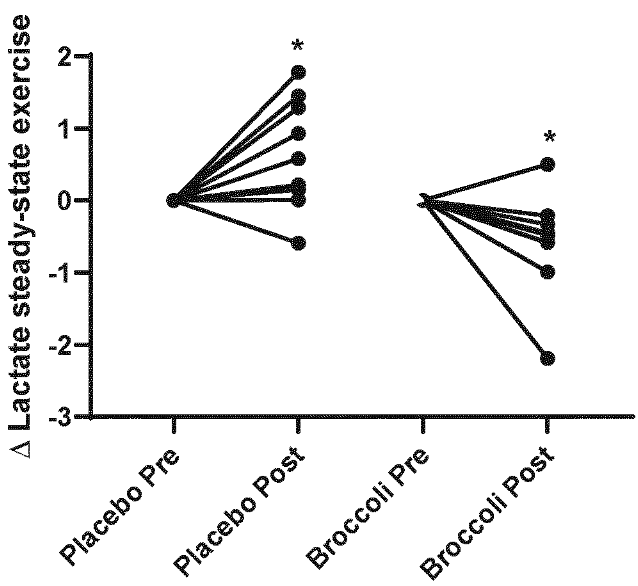

FIG. 4: Effect of chronic administration of BSJ on blood lactate levels in subjects undertaking exercise training FIG. 5A to 5C: Effect of chronic administration of BSJ in subjects undertaking exercise training on (A) maximal power output, (B) total time to exhaustion, and (C) maximal oxygen uptake.

Figure 6:
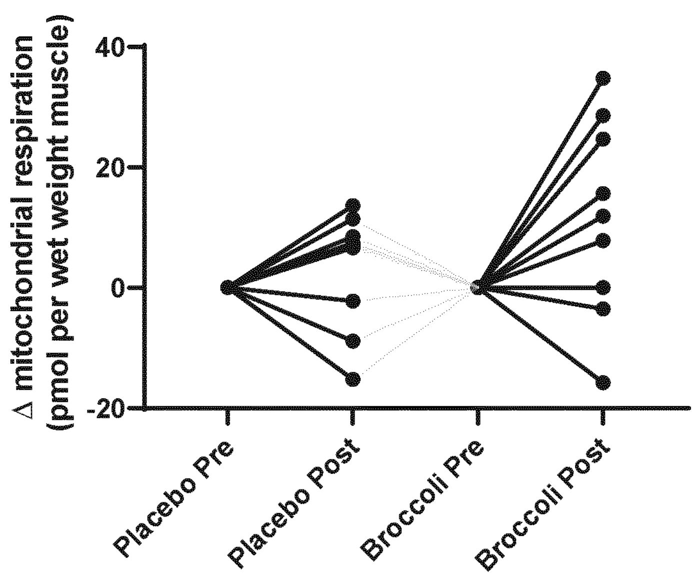

FIG. 6: Effect of chronic administration of BSJ on mitochondrial respiration in subjects undertaking exercise training.

Figure 7:
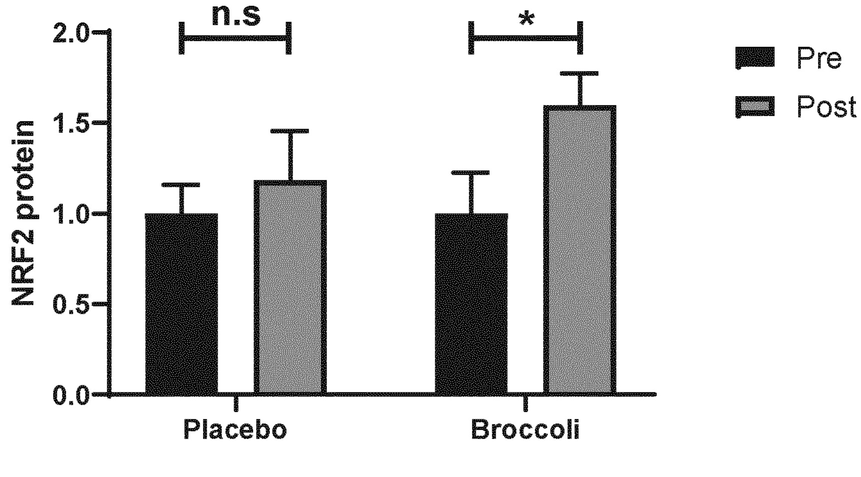

FIG. 7: Effect of chronic administration of BSJ on levels of NRF2 protein present in skeletal muscles in subjects undertaking exercise training.

Figure 8:
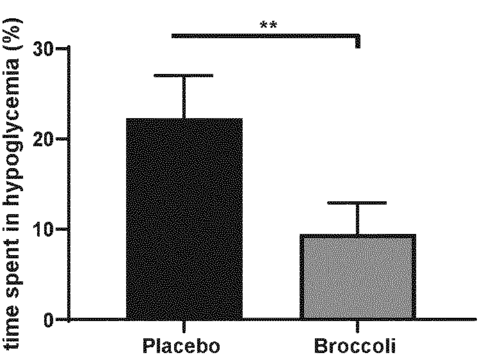

FIG. 8: Effect of chronic administration of BSJ on the time spend in hypoglycaemia in subjects undertaking exercise training.

Figure 9:
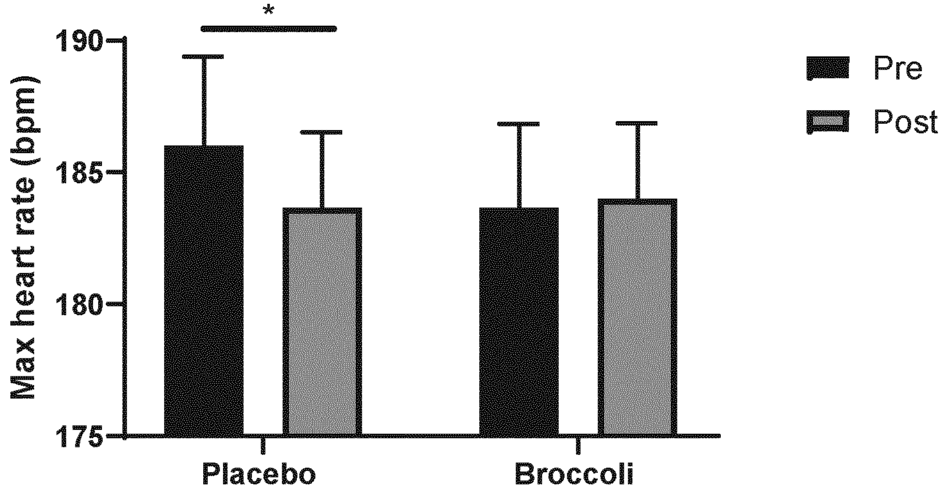

FIG. 9: Effect of chronic administration of BSJ on maximal heart rate during maximum work in subjects undertaking exercise training.

FIG. 10: Overview of conversion of glucosinolates by myrosinase, including the conversion of glucoraphanin to sulforaphane. The glucosinolates glucoraphanin and glucoerucin can be hydrolysed by myrosinase enzymes to give glucose (Glc) and unstable aglycones. These unstable aglycones may form isothiocyanates (e.g. sulforaphane and erucin) and their corresponding nitriles depending on the exact reaction conditions. Furthermore, erucin and sulforaphane can be interconverted (Dinkova-Kostova et al. 2017).

Figure 11:
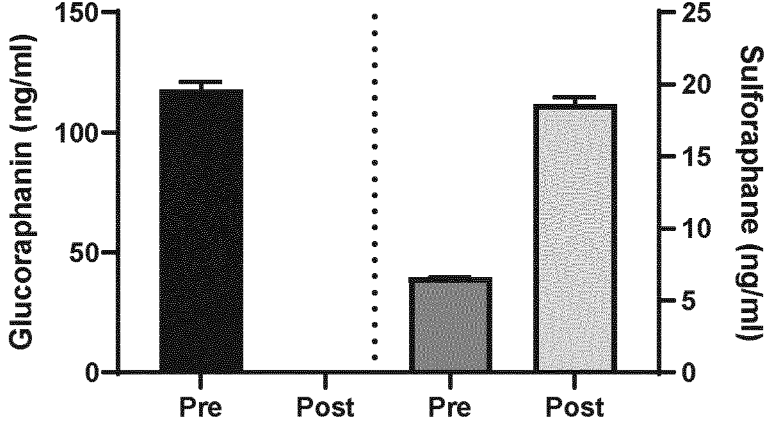

FIG. 11: Conversion of glucoraphanin to sulforaphane in the absence of externally added mustard seeds. Whole sprouts were homogenised in a water solution and kept at room temperature for 14 days. Samples of the homogenate were collected before and after the incubation period and were frozen in liquid nitrogen for later analysis of sulforaphane and glucoraphanin.

EXAMPLES

Study I: Acute Administration of Broccoli Sprout Juice

The aim of study I was to assess blood concentrations of lactate after a single dose i.e. acute administration.

Three healthy male human subjects were enrolled on this study. Subjects were provided compositions of broccoli sprout juice (BSJ) containing broccoli sprouts mixed with mustard seeds and water (2 ml per gram of broccoli sprouts), in the amounts outlined in the table below. A minimum of 48 hours wash-out period was used between administering the different doses within a subject. Five different doses of broccoli sprouts were administered; 0, 10 g, 50 g, 75 g and 150 g.

The total amount of glucosinolates in the broccoli sprouts was assessed according to the methods set out in Meitinger & Kreis, 2018 and was found to be 46 μmol per gram fresh weight. The amount of glucoraphanin and glucoiberin were analyzed using a UPLC-mass spectrophotometric method and found to be 2.3 and 0.15 μg/gram tissue weight, respectively. Peak detection showed particularly high amounts of gluconapin were present in the broccoli sprouts and suggested that gluconapin was the most abundant glucosinolate in the sprouts. The same type of broccoli sprouts were used in studies I, II and II.

| Composition | Broccoli sprouts (g) | Powdered brown mustard seeds (g) | Water (ml) |
|---|---|---|---|
| A | 0 | 0 | — |
| B | 10 | 0.1 | 20 |
| C | 50 | 0.5 | 100 |
| D | 75 | 0.75 | 150 |
| E | 150 | 1.5 | 300 |

Before the consumption of the BSJ, a pre-test was conducted where the subjects cycled on a stationary cycle ergometer at 2 work rates for 5 minutes per work rate at an intensity corresponding to 65 and 80% of maximal oxygen consumption. A capillary blood sample was taken from a punctured fingertip and assessed for lactate. Immediately following the pre-test, the BSJ was consumed by the subject and an identical exercise test was performed 3-3.5 hours after.

The blood lactate was measured both in blood from the capillaries of a punctured finger-tip. The lactate was measured using an enzymatic method using a Biosen C-line lactate analyser.

As shown in FIG. 1, BSJ had an acute effect on blood lactate concentration after submaximal exercise. Surprisingly, the dose-response curve was U-shaped with 10, 50 and 75 grams of BSJ significantly reducing blood lactate concentrations, while 150 grams of BSJ significantly increased blood lactate concentrations (1-way ANOVA). The reduction in blood lactate at the 10-gram dose was 9.6%, at the 50-gram dose was 22%, at the 75-gram dose it was 18% lower, while it was 28% higher at the 150-gram dose. The changes in blood lactate levels are relative to the blood lactate level measured during the pre-test phase.

The distinct U-shaped dose response curve suggests a bimodal use of BSJ during exercise training. A lower blood lactate concentration during submaximal work is a classic positive adaptation to a period of exercise training indicative of enhanced mitochondrial oxidation of pyruvate. The magnitude of decrease in blood lactate at the 50 and 75 gram doses are similar to what can be expected after several weeks of endurance training (Mayes et al. 1987) and are expected to be associated with an improved physical performance. Decreasing lactate accumulation with the pharmacological agent dichloroacetate acutely improves performance (Ludvik et al, 1993).

The 150 grams dose of BSJ significantly increased blood lactate levels during submaximal exercise. This indicates a lowering of mitochondrial oxidation of pyruvate and should be negative for exercise capacity acutely. However, lactate has also been shown to have signalling properties during exercise and elevated lactate levels have been associated with positive long-term adaptations to exercise training (Hashimoto et al 2007).

Study II—Chronic Administration of Broccoli Sprout Juice or a Placebo for 7 Days Six healthy human subjects (4 females, 2 males) were enrolled to participate in a double-blind study into the effects of chronic administration of broccoli sprout juice. Four of the subjects were given broccoli sprout juice (BSJ) and the other two received juice containing an equal amount of juice containing alfalfa sprouts, which contained no glucoraphanin or sulforaphane. The subjects taking alfalfa juice can be used as a negative control.

The juices were administered twice a day (a total dose of 150 g of sprouts daily) for 7 days, with each dose containing 75 g of broccoli or alfalfa sprouts and 150 ml of water. To each juice, 0.75 g of powdered brown mustard seeds were added before consumption to enhance the myrosinase activity and thereby sulforaphane content. The last dose was taken 90 minutes before the exercise test.

Before and after the supplementation period comprehensive physiological tests (outlined below) were performed with metabolic measurements of oxygen uptake, substrate oxidation and assessment of blood lactate formation during incremental submaximal and maximal exercise. Subjects were instructed to maintain their regular lifestyle and did not participate in any regular exercise training. The pre-tests were performed before the supplementation period started and the post-test was done 90 minutes after the last dose (75 grams) of juice was taken.

Physiological Testing

The following physiological tests were performed on the human subjects. For inclusion and assessment of baseline physiological characteristics during cycling, a pre-test was performed on a SRM ergometer (Schoberer Rad Messtechnik, SRM, Jülich, Germany). For assessment of the physiological response to submaximal work rate a standard protocol was used which comprised of a series of five minutes long intervals separated with one minutes of rest where capillary blood lactate and glucose were taken and analyzed using a Biosen C-Line Clinic (EKF-diagnostics, Barleben, Germany). The work rate was set individually at 80-100 W at the first stage and thereafter increased with 15-30 W per stage until a substantial blood lactate accumulation was evident. After a short rest, an incremental maximal exercise test was initiated to determine $VO_2$max. The test started at the work rate of the previous stage, and increased with 20-30 $W \cdot min^{-1}$ until fatigue. $VO_2$max were expressed as the average of the four consecutive highest 10-second long periods. Breath by breath sampling of gas exchange were performed during the entire session using an Oxycon Pro device (Erich Jaeger GmbH, Hoechberg, Germany). Heart rate was measured continuously (Polar Electro OY, Kempele, Finland) and the subjects rated their perceived exertion using the BORG scale (Borg, 1982) at every stage and at exhaustion. The equipment was calibrated according to manufactures instructions.

As shown in FIG. 2, blood lactate concentrations were higher at submaximal work in BSJ group but not in the placebo (alfalfa) group. Despite the higher blood lactate concentration during submaximal exercise, the maximal attainable workload during incremental exercise to exhaustion was unchanged between pre and post testing (see FIG. 3), indicating that positive adaptations to the increased lactate levels had occurred.

Lactate has been shown to have important signalling properties during exercise and elevated lactate levels have been associated with positive long-term adaptations to exercise training (Hashimoto et al. 2007).

Study III: Chronic Administration of Broccoli Sprout Juice or a Placebo in Combination with Exercise Training In this study, nine healthy recreationally active subjects (6 females, 3 males, age 25+/−4 years) were enrolled. The study was a double-blinded, randomized, placebo controlled, cross-over study with 4 weeks wash-out between the interventions. A battery of physiological tests (outlined below) similar to those used in study II were performed prior to the supplementation period.

Similarly to study II, subjects received 2×75 g of BSJ (active) or alfalfa sprouts (placebo) daily, i.e. a total daily dose of 150 g of sprouts, for 10 days. A dose was taken 90 minutes before the subjects donated the muscle biopsy and the last dose was taken 90 minutes before the exercise test on the 10th day. In parallel with the supplementation, subjects performed supervised daily high-intensity interval training at >90% of maximal oxygen consumption for 7 days (outlined below). On day 8, 9 and 10 the subjects continued the supplementation but rested from the training.

Physiological Testing

For inclusion and assessment of baseline physiological characteristics during cycling, a pre-test was performed on an SRM ergometer (Schoberer Rad Messtechnik, SRM, Jülich, Germany). For assessment of the physiological response to submaximal work rate a standard protocol was used which comprised of a series of five minutes long intervals separated with one minutes of rest where capillary blood lactate and glucose were taken and analyzed using a Biosen C-Line Clinic (EKF-diagnostics, Barleben, Germany). The work rate was set individually at 80-100 W at the first stage and thereafter increased with 15-30 W per stage until a substantial blood lactate accumulation was evident. After a short rest, an incremental maximal exercise test was initiated to determine $VO_2$max. The test started at the work rate of the previous stage, and increased with 20-30 $W \cdot min^{-1}$ until fatigue. $VO_2$max were expressed as the average of the four consecutive highest 10-second long periods. Breath by breath sampling of gas exchange were performed during the entire session using an Oxycon Pro device (Erich Jaeger GmbH, Hoechberg, Germany). Heart rate was measured continuously (Polar Electro OY, Kempele, Finland) and the subjects rated their perceived exertion using the BORG scale (Borg, 1982) at every stage and at exhaustion. The equipment was calibrated according to manufactures instructions.

Training Intervention

All physiological tests and HIIT sessions were carefully supervised by highly experienced personnel with extensive background in physiological and performance testing. Subjects were blinded to their performance during HIIT sessions throughout the intervention and were instructed to perform all sessions with the ambition to produce the highest possible mean power output. The intervention period consisted of daily HIIT-sessions (5×4 min at 95% VO2max or 5×8 min at 90% VO2max 4 of the HIIT-sessions were ended with up to 4 30 sec sprints at all-out effort) for 7 days in a row at under close surveillance and careful monitoring of power output and heart rate. The subjects were blinded to power output, cadence and heart rate during all HIIT sessions. All HIIT sessions started with a submaximal warm up of 10 minutes at 100 W and 70 rpm. The subjects were instructed to perform all HIIT sessions to achieve the highest possible mean power output over all intervals. In order to help the subjects with a recommended (standardized) pacing strategy they were paced at the first interval at a power output corresponding to their previously highest measured mean power during a HIIT session.

Nutritional Intervention

After each HIIT session a recovery drink containing 1 g $kg^{-1}$ bw of carbohydrates and 0.25 g $kg^{-1}$ bw of protein was ingested by the subjects. After the last HIIT session, subjects were supplied with an evening meal consisting of 74 g carbohydrates, 38 g protein and 26 g fat that was consumed two hours post exercise. They thereafter remained fasted and reported to the laboratory in early morning for donation of a muscle biopsy.

On day 8, 9 and 10 the subjects continued the supplementation but rested from the training. On the morning of the 8th day a skeletal muscle biopsy was donated and on the 10th day a battery with physiological tests identical to the pre-tests was performed.

Muscle Biopsies

All biopsies were collected in fasted state in early morning following 14 hour of rest after the last HIIT-session. Biopsies were taken from the vastus lateralis. First, local anestethsia (2% Carbocain, AstraZeneca, Sodertalje, Sweden) was injected at the biopsy site. A small incision was made and approximately 150 mg of wet tissue was removed with a Weil-Blakesley chonchotome or a 4 mm Bergstrom needle with manually applied suction. The muscle samples were blotted and dissected clean from visual fat, connective tissue and blood and divided in to three portions; ~50 mg to ice cold ISO-medium for respirometrics and two portions of 50-100 mg to liquid nitrogen and thereafter stored in −80° C. for later analysis.

Mitochondrial Isolation and Respirometry

Mitochondria were isolated from ~50 mg of musclein isolation medium (Sucrose 100 mM, KCl 100 mM, Tris-HCl 50 mM, $KH_2PO_4$ 1 mM, EGTA 100 μM, BSA 0.1%; pH 7.4 as described by Gnaiger and Kuznetsov, 2002). Muscle was kept on ice and homogenized first by scissors and thereafter after addition of 0.2 mg $ml^{-1}$ bacterial protease, further homogenization was performed in a water-cooled glass homogenizer. The homogenate was centrifuged at 700 rcf at 4° C. for 10 min in a 15 ml tube and the supernatant was transferred to new 1.5 ml tubes and centrifuged at 10000 g at 4° C. The pellets were resolved and transferred to a single 1.5 ml tube and centrifuged at 7000 rcf at 4° C. for 5 min giving a resultant pellet that was liquated in 0.6 μl per initial mg wet weight of muscle in preservation medium (EGTA 0.5 mM, MgCl2 6H2O 3 mM, K-lactobionate 60 mM, Taurine 20 mM, $KH_2PO_4$ 10 mM, HEPES 20 mM, Sucrose 110 mM, BSA 1 g $L^{-1}$ Histidine 20 mM, Vitamin E succinate 20 μM, Glutathione 3 mM, Leupeptine 1 μM, Glutamate 2 mM, Malate 2 mM, Mg-ATP 2 mM).

Mitochondrial respiration were measured using a two-channel high-resolution respirometer (Oxygraph-2k, Oroboros Instruments Corporation, Innsbruck, Austria). 5 ul of isolated mitocondria were added to two 2 ml wells containing respiration medium MIR05 (EGTA 0.5 mM, MgCl2·6H2O 3 mM, K-lactobionate 60 mM, Taurine 20 mM, KH2PO4 10 mM, HEPES 20 mM, Sucrose 110 mM, BSA 1 g L-1). All experiments were performed at 37° C. and 02 calibration calibration was performed according to the manufactures' instructions. All measurements were performed and analyzed in DatLab 5.2 software (Oroboros, Paar, Graz, Austria). Mitochondrial respiration was related to the wet weight of the initial piece of muscle before mitochondrial isolation.

Immunoblotting

Homogenization was performed in freeze dried samples of ~2 mg muscle. The protocol for homogenization is extensively described earlier (Samuelsson et al., 2016). Briefly, 100 μl/mg dry WT of homogenization buffer consisting of 2 mM HEPES (pH 7.4), 1 mM EDTA, 5 mM EGTA, 10 mM MgCl2, 50 mM β-glycerophosphate, 1% Triton X-100, 1 mM $Na_3VO_4$, 2 mM dithiothreitol, 1% phosphatase inhibitor cocktail (Sigma P-2850) and 1% (vol/vol) Halt Protease Inhibitor Cocktail (Thermo Scientific, Rockford, IL) was added to each sample and processed in a bullet blender until homogenized. After rotation for 30 min at 4° C. and centrifugation at 10,000 g for 10 min at 4° C. the supernatant was analysed for protein content and diluted with homogenization buffer and Laemmli buffer (Bio-Rad, Richmond, CA) obtaining a protein concentration of 1 μg/μl. All samples were denatured at 95° C. for five minutes and stored at −80° C.

Samples of muscle homogenates 20, 16 or 14 μg of protein were loaded to 26-well Criterion TGX gradient gels (4-20% acrylamide; Bio-Rad). Electrophoresis (300 V for 32 minutes kept on ice) were performed in transfer buffer containing 25 mM Tris base, 192 mM glycine, and 10% methanol and the proteins were then transferred to a polyvinylidine fluoride membranes (Bio-Rad) at a constant current of 300 mA for 3 h kept on ice. The membranes were stained with MemCode Reversible Protein Stain Kit (Thermo Scientific) as a loading control. The membranes were then destained and blocked with Tris-buffered saline (TBS; 20 mM Tris base, 137 mM NaCl, pH 7.6) containing 5% non-fat dry milk for 1 h at room temperature. Thereafter, incubation overnight followed with antibodies diluted with TBS buffer with 2.5% non-fat dry milk and 0.1% Tween. The antibody used was from Cell Signaling Technology; Nrf2 (D1Z9C). After incubation, the membranes were washed and incubated with secondary antibodies conjugated with horseradish peroxidase 1 h at room temperature. The membranes were washed again and Super Signal West Femto Chemiluminescent Substrate (Thermo Scientific) was added and target protein visualized and quantified in Molecular Imager ChemiDoc XRS system with Quantity One software (version 4.6.3; Bio-Rad) and in ChemiDoc MP with Quantity One software (version 6.0.1; Bio-Rad).

Glucose Monitoring

Furthermore, the subjects wore a continuous glucose monitor (a skin-mounted sensor (FreeStyle Libre, Abbot)) throughout the supplementation period that measured interstitial glucose concentrations every 15 minutes. The sensor was fitted laterally on the subject's deltoideus and automatically stored measurements for a maximum of eight hours before it had to be emptied using a portable reader. If the sensor failed to measure, or if the subject did not export data from the sensor to the reader within eight hour from the last export, the sensor overwrites previously stored data and leave a gap in the exported text fil. The first 12 hours of measurements were also excluded from all subjects due to differences in time before readings appeared stable.

After 4 weeks of wash-out the procedure was repeated but the subjects that first received BSJ now received placebo and vice versa.

As shown in FIG. 4, blood lactate concentrations at submaximal workloads (50-75% of VO2max) increased significantly after training in the placebo group and decreased significantly in the BSJ condition. The classical adaptation to endurance exercise training is a decreased lactate concentration at submaximal workloads due to enhanced mitochondrial respiration and better aerobic capacity. The increased lactate concentrations in the placebo condition may be interpreted as a maladaptation to the intense training load, whereas in the BSJ condition the subjects' ability to adapt to the workload was enhanced.

Figure 5:
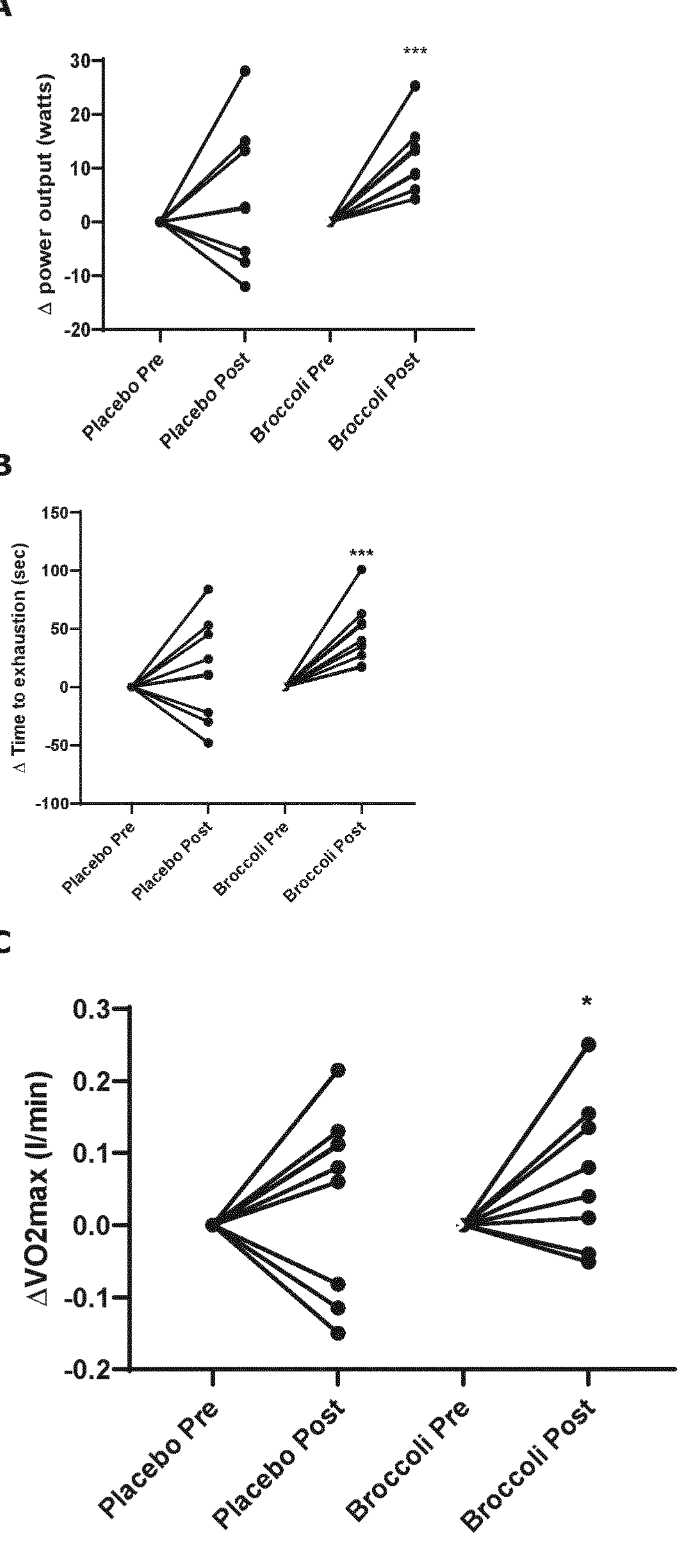

Subjects performed an incremental exercise protocol to exhaustion to determine maximal power output, time to exhaustion and $VO_2$max. As shown in FIG. 5A, the maximum power output at exhaustion was significantly enhanced in the BSJ condition only and all subjects experienced an increase in maximal power output. The response in the placebo condition was not significant with 3 subjects showing adverse responses to the training stimuli (FIG. 5A).

As shown in FIG. 5B, the time to exhaustion during the same incremental exercise protocol was significantly increased in the BSJ condition only, with all subjects experiencing an increase in the amount of time taken to exhaustion. The response in the placebo condition was not significant with some subjects experiencing a decrease in their time to exhaustion (FIG. 5B).

As shown in FIG. 5C, maximal oxygen uptake was significantly increased in the BSJ condition. Furthermore, there were a greater number of adverse responders in the placebo condition.

The results in FIGS. 5A to 5C suggest that positive adaptations to physical exercise have taken place in those subjections consuming BSJ and experiencing the decreased lactate concentration.

A muscle biopsy was taken pre and post each supplementation condition. The expected response after a training period is that mitochondrial respiration should increase. No effect on mitochondrial respiration in the placebo group but a tendency (p=0.067) towards an improvement was observed in the BSJ condition (FIG. 6).

Nrf2 protein abundance in the skeletal muscle biopsy was assessed using western blotting technique. We found that nrf2 was significantly increased in the BSJ condition but not in the placebo condition. Induction of nrf2 by sulforaphane or broccoli sprouts in skeletal muscle is a novel finding (FIG. 7).

Additionally, the inventors found that nrf2 indeed was increased after consumption of compositions comprising sulforaphane and/or myrosinase and/or glucoraphanin (e.g. broccoli sprout juice) but not after the placebo condition. nrf2 can also be activated by exercise (Done & Traustadóttir, 2016) and this is an important part of the muscle cell's ability to withstand higher oxidative load and adapt to a higher metabolic requirement, i.e. improve physical performance. There are indications that the activation of nrf2 from sulforaphane and physical exercise occurs through different mechanisms, which consequently there may be synergistic effects between sulforaphane intake and exercise.

Intensive physical exercise releases a large amount of free oxygen radicals (ROS) that needs to be effectively scavenged by the muscle cell. Furthermore, oxidative stress has also been shown to be linked to the aging process and several pathological conditions (Lu et al, 2004). However, in the context of exercise, this oxidative stress has been shown to be necessary for the initiation of the body's adaptation processes and will ultimately lead to a better physical performance (Ristow et al 2009). Conversely, we have recently shown that excessive physical exercise leads to a ROS load that the cell's antioxidant defenses cannot handle, ultimately leading to inhibited mitochondrial function and oxidative damage at the cellular level (Larsen et al, 2016). It is clearly conceivable that supplementation with broccoli sprouts can stimulate this antioxidant defence by activating nrf2 in skeletal muscle and ultimately lead to better performance and better resistance to intensive exercise that has been partially found in animal studies (Malaguti et al, 2009).

Periods of very intense exercise training are typically associated with adverse responses such as an increase in nocturnal hypoglycaemic episodes and a reduction in maximal heart rate. To assess whether BSJ could protect against these adversities, blood glucose concentrations were monitored using continuous glucose monitors (CGMs) during the supplementation period. The time spent in the hypoglycaemic range was significantly reduced in the BSJ condition as compared to the placebo condition (FIG. 8). During the placebo condition the subjects spent 22% of their time (more than 5 hours per day) in the hypoglycaemic range while during the broccoli condition this was reduced to only 9%.

BSJ enhances the resistance to a period of very hard training, presumably through activation of nrf2 and modulation of lactate levels during exercise. The clear dose-response effect on blood lactate levels during submaximal exercise is both novel and surprising. The inventors are not aware of any other nutritional supplement that has this effect. A decrease in lactate levels during exercise is the hallmark of positive training adaptations to an endurance training program. In athletes, lactate levels are more sensitive to changes in fitness level than VO2max that usually remains fairly constant over time in already highly trained subjects.

Furthermore, maximum heart rate during maximal work was significantly reduced in the placebo condition but was maintained in the BSJ condition (FIG. 9).

Study IV: Effect of Mustard Seeds on Sulforaphane Formation from Glucoraphanin

The inventors conducted a study to determine whether any physiological effects might be produced by BSJ in the absence of myrosinase provided in the form of mustard seeds.

Frozen sprouts were thawed, homogenised and left in room temperature (20 degrees Celsius) to assess the formation of sulforaphane without adding myrosinase-rich mustard seeds. Glucoraphanin and sulforaphane were assessed before and after 14 days incubation at 20 degrees Celsius. During incubation glucoraphanin concentrations declined from 118.1 to 6.6 g/l, while sulforaphane increased from 0.09 to 18.6 g/I indicating abundant myrosinase activity in the sprout homogenate. Glucoraphanin and sulforaphane were analysed using UPLC mass spectrometry with both positive and negative ionization.

Sulforaphane levels generated from the conversion of glucoraphanin in the absence of myrosinase from mustard seeds were measured (FIG. 11). The myrosinase activity in frozen BSJ is enough to hydrolyse all glucoraphanin into sulforaphane.

REFERENCES

Abukhabta S, et al. Sulforaphane-enriched extracts from glucoraphanin-rich broccoli exert antimicrobial activity against gut pathogens in vitro and innovative cooking methods increase in vivo intestinal delivery of sulforaphane. Eur J Nutr. 2020 Jul. 10.

Alumkal J J, et al. A phase II study of sulforaphane-rich broccoli sprout extracts in men with recurrent prostate cancer. Invest New Drugs 2015—Clinical Trial. PMID 25431127.

Cardinale D A, Gejl K D, Ortenblad N, Ekblom B, Blomstrand E, Larsen F J. Reliability of maximal mitochondrial oxidative phosphorylation in permeabilized fibers from the vastus lateralis employing high-resolution respirometry. Physiol Rep. 2018 February; 6(4):e13611.

Clarke J D, Riedl K, Bella D, Schwartz S J, Stevens J F, Ho E. Comparison of isothiocyanate metabolite levels and histone deacetylase activity in human subjects consuming broccoli sprouts or broccoli supplement. 3 Agric Food Chem. 2011 Oct. 26; 59(20):10955-63. doi: 10.1021/jf202887c. Epub 2011 Sep. 30.

Dinkova-Kostova et al. KEAP1 and done? Targeting the NRF2 pathway with sulforaphane. Trends Food Sci Technol. 2017 November; 69(Pt B):257-269

Done & Traustadottir, Aerobic exercise increases resistance to oxidative stress in sedentary older middle-aged adults. A pilot study. Age (Dordr) 2016 December; 38(5-6):505-512. doi: 10.1007/s11357-016-9942-x. Epub 2016 Aug. 25.

Hashimoto T, Hussien R, Oommen S, Gohil K. Brooks G A. Lactate sensitive transcription factor network in L6 cells: activation of MCT1 and mitochondrial biogenesis. FASEB J. 2007; 21:2602-2612.

Larsen F J, Schiffer T A, Ørtenblad N, Zinner C, Morales-Alamo D, Willis S J, Calbet J A, Holmberg H C, Boushel R. High-intensity sprint training inhibits mitochondrial respiration through aconitase inactivation. FASEB J. 2016 January; 30(1):417-27

Larsen S, Nielsen J, Hansen C N, Nielsen L B, Wibrand F, Stride N, Schroder H D, Boushel R, Helge J W, Dela F, Hey-Mogensen M. Biomarkers of mitochondrial content in skeletal muscle of healthy young human subjects. 3 Physiol. 2012 Jul. 15; 590(14): 3349-60.

López-Chillon M T, et al. Effects of long-term consumption of broccoli sprouts on inflammatory markers in overweight subjects Clin Nutr 2019. PMID 29573889

Lu T, Pan Y, Kao S Y, Li C, Kohane I, Chan J, Yankner B A. Gene regulation and DNA damage in the ageing human brain. Nature. 2004 Jun. 24; 429(6994):883-91. Epub 2004 Jun. 9.

Ludvik B, G Mayer G et al. Effects of dichloroacetate on exercise performance in healthy volunteers. Pflugers Arch. 1993 May; 423(3-4):251-4

Malaguti M, Angeloni C, Garatachea N, Baldini M, Leoncini E, Collado P S, Teti G, Falconi M, Gonzalez-Gallego J, Hrelia S. Sulforaphane treatment protects skeletal muscle against damage induced by exhaustive exercise in rats. J Appl Physiol (1985). 2009 October; 107(4):1028-36.

Mayes R, Hardman A E, Williams C. The influence of training on endurance and blood lactate concentration during submaximal exercise. Br J Sports Med 1987 September; 21(3): 119-24.

Meitinger N, Kreis W. Development and validation of a quick assay for the total glucosinolate content in horseradish (*Armoracia rusticana*) using glucose strips and a blood glucose meter. Journal of Applied Botany and Food Quality 91, 232-236 (2018)

Oh S, et al. Nuclear factor (erythroid derived 2)-like 2 activation increases exercise endurance capacity via redox modulation in skeletal muscles. Sci Rep 2017. PMID 29018242

Poffé C., et al. Ketone ester supplementation blunts over-reaching symptoms during endurance training overload 3 Physiol. 2019 Jun. 15; 597(12): 3009-3027.

Remington: *The Science and Practice of Pharmacy,* $19^{th}$ ed., vol. 1 & 2 (ed. Gennaro, 1995, Mack Publishing Company).

Ristow M, Zarse K, Oberbach A, Klating N, Birringer M, Kiehntopf M, Stumvoll M, Kahn C R, Blüher M. Antioxidants prevent health-promoting effects of physical exercise in humans. Proc Natl Acad Sci USA. 2009 May 26; 106(21):8665-70. doi: 10.1073/pnas.0903485106. Epub 2009 May 11.

Singh K, et al. Sulforaphane treatment of autism spectrum disorder (ASD). Proc Natl Acad Sci USA 2014—Clinical Trial. PMID 25313065

Sunderland et al. Exercise and adrenaline increase PGC-1α mRNA expression in rat adipose tissue. J Physiol. 2009 Apr. 1; 587(Pt 7): 1607-1617.

Wilkinson A P, Rhodes M J, Fenwick G R. Determination of myrosinase (thioglucoside glucohydrolase) activity by a spectrophotometric coupled enzyme assay. Anal Biochem. 1984 June; 139(2):284-91.

Wise R A, et al. Lack of Effect of Oral Sulforaphane Administration on Nrf2 Expression in COPD: A Randomized, Double-Blind, Placebo Controlled Trial. PLoS One 2016—Clinical Trial. PMID 27832073

The invention claimed is:

1. A method of increasing blood lactate concentration during physical exercise in a human subject, comprising orally administering to the human subject, less than six hours before the exercise, a composition comprising an effective amount of (i) sulforaphane, (ii) glucoraphanin and myrosinase, (iii) sulforaphane and myrosinase, or (iv) sulforaphane, glucoraphanin and myrosinase, with the proviso that when the composition comprises glucoraphanin it further comprises myrosinase; wherein, at a matched workload, the human subject's blood lactate concentration is higher relative to when the same human subject performs the exercise without having been administered the composition.

2. The method according to claim 1, wherein the human subject is administered a composition comprising sulforaphane.

3. The method according to claim 1, wherein the human subject is administered a composition comprising glucoraphanin and myrosinase.

4. The method according to claim 1, wherein the human subject is administered a composition comprising sulforaphane, glucoraphanin and myrosinase.

5. The method according to claim 2, wherein the composition is for oral administration, and is administered orally to the human subject by direct ingestion, buccal administration, or sublingual administration.

6. The method according to claim 5, wherein, the composition is in a tablet, a capsule, a lozenge, a chewing gum, a solution, an elixir or a suspension.

7. The method according to claim 1, wherein the composition is administered once acutely in a single dose.

8. The method according to claim 7, wherein the composition is administered to the human subject less than five hours before; or less than three hours before; or less than two hours before; or less than one hour before physical exercise, or about 90 minutes before physical exercise.

9. The method according to claim 8, wherein the composition is in a juice form in an amount equivalent to that produced by 150 grams of fresh broccoli sprouts.

10. The method of claim 9, wherein the juice comprises homogenized broccoli sprouts and water.

11. The method according to claim 1, wherein the composition is administered daily, for a period of at least two days.

12. The method according to claim 11, wherein the composition is further administered daily, for a period of three days, or four days, or five days, or six days, or seven days, or two weeks, or three weeks, or four weeks, or one month.

13. The method according to claim 1, wherein the composition comprises sulforaphane and/or glucoraphanin in the form of at least 150 grams of broccoli sprouts.

14. The method according to claim 1, wherein the subject exhibits improved physical exercise relative to when the subject performs the same exercise without the composition, wherein the improved exercise performance comprises increased time-to-exhaustion at a constant workload, increased mechanical power output, or increased maximal oxygen uptake ($VO_2$max).

15. The method according to claim 14, wherein the improved physical exercise comprises one or more of increased time-to-exhaustion at a constant workload, increased mechanical power output, or increased maximal oxygen uptake ($VO_2$max).

16. The method of claim 1, wherein the source of sulforaphane and/or glucoraphanin is selected from the group consisting of: broccoli sprouts or an extract thereof; mature broccoli or an extract thereof; Brussels sprouts or an extract thereof; kale sprouts or an extract thereof; kale or an extract thereof; cabbage or an extract thereof; cabbage sprouts or an extract thereof; cauliflower or an extract thereof; cauliflower sprouts or an extract thereof; broccoli raab or an extract thereof; broccoli raab sprouts or an extract thereof; red kale or an extract thereof; red kale sprouts or an extract thereof; kohlrabi or an extract thereof; kohlrabi sprouts or an extract thereof; and red mizuna or an extract thereof; red mizuna sprouts or an extract thereof.

17. The method of claim 16, wherein the total amount of glucosinolates in the broccoli sprouts is about 46 μmol per gram fresh weight.

18. The method of claim 16, wherein the amounts of glucoraphanin and glucoiberin in the broccoli sprouts are about 2.3 μg per gram tissue weight and about 0.15 μg per gram tissue weight, respectively.

19. The method of claim 18, wherein the amount of broccoli sprouts administered is at least 150 g per day.

20. The method of claim 1, wherein the source of myrosinase is selected from the group consisting of: brown mustard seeds or an extract thereof; white mustard seeds or an extract thereof; yellow mustard seeds or an extract thereof; rocket (arugula) or an extract thereof;

rocket seeds or an extract thereof; rocket sprouts or an extract thereof; garden cress or an extract thereof; garden cress seeds or an extract thereof; garden cress sprouts or an extract thereof; wasabi or an extract thereof; wasabi seeds or an extract thereof; wasabi sprouts or an extract thereof; daikon or an extract thereof; daikon seeds or an extract thereof; daikon sprouts or an extract thereof; horseradish or an extract thereof; horseradish seeds or an extract thereof; horseradish sprouts or an extract thereof; radish or an extract thereof; radish seeds or an extract thereof; radish sprouts or an extract thereof; and purified or isolated myrosinase.

21. The method of claim 1, wherein the matched workload is defined as a mechanical power output within +5% of a baseline value for the subject.

22. The method of claim 1, wherein blood lactate concentration is measured by an enzymatic assay using capillary or venous blood.

23. The method according to claim 1, wherein the human subject is administered a composition comprising sulforaphane and myrosinase.

24. The method according to claim 1, wherein the human subject is administered a composition comprising sulforaphane, glucoraphanin, and myrosinase.

* * * * *